US009370616B2

(12) United States Patent
Nakash et al.

(10) Patent No.: US 9,370,616 B2
(45) Date of Patent: Jun. 21, 2016

(54) CONTINUOUS AND CONTROLLED IRRIGATION SYSTEM

(75) Inventors: Ehood Nakash, Petah Tikva (IL); Eliahu Eliachar, Haifa (IL); Lilach Nir, Kfar Yehoshua (IL); Ram Grossfield, Haifa (IL); Gil Tenennbaum, Modiin (IL); Izak Orbach, Kadima (IL)

(73) Assignee: FLOW MED LTD., Petah Tikva (IL)

( * ) Notice: Subject to any disclaimer, the term of this patent is extended or adjusted under 35 U.S.C. 154(b) by 214 days.

(21) Appl. No.: 14/008,684

(22) PCT Filed: Mar. 29, 2012

(86) PCT No.: PCT/IL2012/000138
§ 371 (c)(1),
(2), (4) Date: Jan. 28, 2014

(87) PCT Pub. No.: WO2012/131674
PCT Pub. Date: Oct. 4, 2012

(65) Prior Publication Data
US 2015/0126959 A1 May 7, 2015

Related U.S. Application Data

(60) Provisional application No. 61/469,112, filed on Mar. 30, 2011.

(51) Int. Cl.
*A61M 37/00* (2006.01)
*A61M 3/02* (2006.01)
(Continued)

(52) U.S. Cl.
CPC ........... *A61M 3/0258* (2013.01); *A61M 3/0266* (2013.01); *A61M 5/142* (2013.01);
(Continued)

(58) Field of Classification Search
CPC ............. A61M 2205/3379; A61M 2205/3576; A61M 2205/52; A61M 3/0258; A61M 3/0266; A61M 5/1407; A61M 5/142; A61M 5/16827; A61M 5/16877; A61M 5/16881
USPC ........................................................ 604/131
See application file for complete search history.

(56) References Cited

U.S. PATENT DOCUMENTS 5,254,083 A 10/1993 Gentelia et al.
5,348,539 A * 9/1994 Herskowitz ......... A61M 5/1483
604/141

(Continued)

OTHER PUBLICATIONS

International Search Report dated Dec. 24, 2012 in corresponding International Application No. PCT/IL2012000138.

*Primary Examiner* — Kevin C Sirmons
*Assistant Examiner* — Deanna K Hall
(74) *Attorney, Agent, or Firm* — Reches Patents

(57) ABSTRACT

An irrigation system for providing a continuous and controlled flow of a fluid. The system includes (a) a reservoir system having a main longitudinal axis and a plurality of containers of fluid; (b) a fluid transfer system in fluid connection with said reservoir system and includes at least one fluid transfer head, adapted to transfer fluid from one of said plurality of containers to an external tubing system; and (c) at least one connector between said container and said fluid transfer head. Each fluid transfer head has a mechanism adapted to linearly move each of said fluid transfer heads along said main longitudinal axis. Each container comprises a neck and a nipple. Each connector is reversibly coupled to said irrigation system and comprises: a lower section comprising two arcs, the distance between the centers of said arcs substantially equal to the distance between the centers of said neck and said nipple.

18 Claims, 15 Drawing Sheets

(51) Int. Cl.
*A61M 5/14* (2006.01)
*A61M 5/142* (2006.01)
*A61M 5/168* (2006.01)
*A61M 16/01* (2006.01)
*A61M 16/18* (2006.01)
*A61M 19/00* (2006.01)

(52) U.S. Cl.
CPC ........ *A61M 5/1407* (2013.01); *A61M 5/16877* (2013.01); *A61M 5/16881* (2013.01); *A61M 5/16827* (2013.01); *A61M 5/16845* (2013.01); *A61M 16/01* (2013.01); *A61M 16/18* (2013.01); *A61M 19/00* (2013.01); *A61M 2202/0208* (2013.01); *A61M 2205/18* (2013.01); *A61M 2205/3379* (2013.01); *A61M 2205/3393* (2013.01); *A61M 2205/3576* (2013.01); *A61M 2205/502* (2013.01); *A61M 2205/52* (2013.01)

(56) References Cited

U.S. PATENT DOCUMENTS

| | | | |
|---|---|---|---|
| 5,830,180 A * | 11/1998 | Chandler | A61M 3/0258 604/35 |
| 6,923,422 B2 * | 8/2005 | Schmaltz | A61F 5/4405 251/294 |
| 7,499,581 B2 * | 3/2009 | Tribble | B65B 3/003 250/577 |
| 2002/0062123 A1 | 5/2002 | McClurken et al. | |
| 2006/0052666 A1 | 3/2006 | Kumar | |
| 2006/0259195 A1 * | 11/2006 | Eliuk | A61J 1/20 700/245 |
| 2007/0032763 A1 | 2/2007 | Vogel | |
| 2008/0172021 A1 | 7/2008 | Dijkman | |
| 2009/0012449 A1 * | 1/2009 | Lee | A61M 1/28 604/29 |
| 2009/0012453 A1 | 1/2009 | Childers et al. | |
| 2011/0002802 A1 | 1/2011 | Capone et al. | |
| 2011/0004143 A1 | 1/2011 | Beiriger et al. | |

* cited by examiner

CONTINUOUS AND CONTROLLED IRRIGATION SYSTEM

FIELD OF THE INVENTION

This invention relates to means for providing irrigation for surgical procedures in which the fluid is provided with a constant flow. In particular, it relates to such means in which the fluid is provided from a plurality of independent containers.

BACKGROUND OF THE INVENTION

An irrigation system is a system that delivers fluids for a predetermined amount of time and to a predetermined body part/patient in need.

The present invention provides a constant flow of fluid. Such an irrigation system is useful in practically every procedure currently known. Irrigation system are used on patients in the OR (operating rooms), in ER (emergency rooms), in intensive care, in recovery rooms post surgery, and on patients who are admitted in hospital or clinics.

Irrigation is needed in different types medical procedures and operations and while using different types of fluids.

Many kinds of irrigation fluid are used, including, among others, blood, glycine, water, plasma, saline, plasma, drugs.

For example, procedures may require irrigation of oxygen; anesthetic gas for use as local anesthesia, regional anesthesia and general anesthesia selected from ethers, halogenated ethers, desflurane (2,2,2-trifluoro-1-fluoroethyl-difluoromethyl ether, sevoflurane (2,2,2-trifluoro-1-[trifluoromethyl] ethyl fluoromethyl ether), and isoflurane (2-chloro-2-(difluoromethoxy)-1,1,1-trifluoro-ethane); blood; saline; glycine; water; plasma; medicament and any combination thereof.

The following give a few examples of procedures in which glycine, saline, medicaments, or any combinations thereof are required as the irrigation fluid. Many medical procedures such as TURP (transurethral prostatic resection), PCNL, uteroscopy, hysteroscopy etc, require a constant flow of fluid such as saline or glycine in order to wash away blood and resected tissue and to maintain the temperature of the tissue and of the surgical instrument.

In, for example, TURP surgery (Transurethral Resection of the Prostate), the surgeon inserts a Resectoscope into the urethra. The Resectoscope allows the surgeon to see the enlarged prostate gland and to remove a small piece of the prostate gland tissue using the resectoscope's electrical cutting loop.

TURP is a non-invasive surgery that requires a continuous flow of solution (e.g., glycine) to the prostate and bladder and out through the Resectoscope.

The Continuous Irrigation enables the surgeon to:
1. Increase the volume of the prostate & bladder (building a surgical site);
2. Clean blood flow from the prostate; and,
3. Clean resected tissue from the prostate
4. Cool the prostate, removing the heat caused by the electrical cutting loop.

Any discontinuation of the supply of solution immediately results in a drop in the fluid pressure and thus, a "collapse" of the prostate and bladder, accumulation of blood that eventually blocks the surgical view (surgical site), and the accumulation of blood clots, which can stop the surgery and all of which increase the patient's risks.

Thus, it would be advantageous to provide a continuous flow of solution.

The irrigation fluid is generally provided from one or more containers (e.g. solution bags) positioned above the level of the operating table. Fluid flows from the containers through a tube (e.g. disposable Y type set) under gravity to the patient. Each container supplies flow for approximately 10 minutes, then it needs to be manually replaced. These manual procedures suffer from problems such as a high dependence on the medical personal who must notice that the container needs replacing and who must replace the solution bag on time, the limitation of the flow rate, and a lack of means of informing the operators that the solution has run out or is about to run out.

A fully automated system, in which a new container is opened as an old one empties in a fully automated manner without the need of human intervention and in which a notification can be provided to the operator when the solution has run out or if there is a system failure, thus remains a long-felt need.

SUMMARY OF THE INVENTION

The invention disclosed herein is designed to meet this long-felt need. The system and method provide a means by which fluid is provided from a plurality of containers such that as each container empties to a certain level (e.g. to half its initial content), flow is automatically started from a different container, thus maintaining a constant flow through the system.

The present invention provides a unique robotic solution, based on using the solution bags (containers) currently used, with an electro-mechanical system that replaces the manual procedure (namely, switching between containers) with an automatic one.

The system consists of several sub mechanisms; e.g., a mechanism that spikes the bag/container with a disposable or reusable set (tube), a mechanism that builds pressure that creates the flow, a mechanism that identifies the quantity of fluid available in the bag/container and when it is about to be empty, and a mechanism that switches to a new bag/container automatically, spikes it and builds pressure according to the surgeon's needs, thus enabling Continuous Irrigation.

It is one object of the present invention to provide an irrigation system for providing a continuous and controlled flow of a fluid, wherein said system comprises:
a reservoir system comprising a plurality of containers of fluid; said reservoir system characterized by a predetermined configuration;
a fluid transfer system in fluid connection with said reservoir system, said fluid transfer system comprising:
at least one fluid transfer head, adapted to transfer fluid from one of said plurality of containers to an external tubing system; wherein each of said fluid transfer heads is characterized by a mechanism adapted to linearly move each of said fluid transfer heads along said predetermined configuration from one of said containers to another.

It is one object of the present invention to provide an irrigation system for providing a continuous and controlled flow of a fluid, wherein said system comprises:
a reservoir system comprising a plurality of containers of fluid; said reservoir system characterized by a main longitudinal axis;
a fluid transfer system in fluid connection with said reservoir system, said fluid transfer system comprising:
at least one fluid transfer head, adapted to transfer fluid from one of said plurality of containers to an external tubing system; wherein each of said fluid transfer heads is characterized by a mechanism adapted to linearly move each of said fluid transfer heads along said main longitudinal axis.

It is another object of the present invention to provide an irrigation system for providing a continuous and controlled rate flow of a fluid, wherein said system comprises:

a reservoir system comprising a plurality of containers of fluid; said containers in said reservoir system disposed in a predetermined configuration;

a fluid transfer system in fluid connection with said reservoir system, said fluid transfer system comprising:

at least one fluid transfer head, adapted to transfer fluid from one of said plurality of containers to an external tubing system; wherein each of said fluid transfer heads is characterized by a mechanism adapted to radially move each of said fluid transfer heads.

It is another object of the present invention to provide the irrigation system as defined above, wherein said predetermined configuration is selected from a group consisting of a linear configuration, a radial configuration, an ellipsoidal configuration, a square configuration, a triangular configuration, a hexagonal configuration, a pentagonal configuration, a configuration of any 2D or 3D shape and any combination thereof.

It is another object of the present invention to provide the irrigation system as defined above, wherein said fluid transfer system further comprising fluid regulating means, adapted to regulate either the rate of transfer of fluid from said reservoir system to each of said fluid transfer heads or the pressure at which said fluid is transferred from said reservoir system to each of said fluid transfer heads.

It is another object of the present invention to provide the irrigation system as defined above, wherein said system further comprising a control system adapted to control at least one selected from a group consisting of (a) the rate of flow of fluid through said irrigation system according to a predetermined protocol; (b) the movement of said at least one fluid transfer head; (c) the activation of said at least one fluid transfer head; and any combination thereof.

It is another object of the present invention to provide the irrigation system as defined above, wherein said system further comprising a pressure building system selected from pumping means adapted to withdraw said fluid from at least one of said containers; or pressure applying means adapted to apply pressure on at least one of said containers.

It is another object of the present invention to provide the irrigation system as defined above, wherein said system further comprising a pumping system in fluid connection with said fluid transfer system, adapted to withdraw said fluid from at least one of said containers of fluid at a predetermined rate of flow to an outer tubing system.

It is another object of the present invention to provide the irrigation system as defined above, wherein said system further comprising pressure applying means adapted to apply pressure on at least one of said containers of fluid so as to enable a predetermined rate of flow from at least one of said containers to an outer tubing system.

It is another object of the present invention to provide the irrigation system as defined above, wherein said pressure applying means is selected from a group consisting of a membrane encapsulating at least one of said containers of fluid, squeezing means adapted to apply squeezing pressure on at least one of said containers and any combination thereof and any combination thereof.

It is another object of the present invention to provide the irrigation system as defined above, wherein said squeezing means are selected from pneumatic compression of at least one of the containers, hydrostatic compression of at least one of the containers and any combination thereof.

It is another object of the present invention to provide the irrigation system as defined above, wherein said fluid is selected from a group consisting of gas, liquid and any combination thereof.

It is another object of the present invention to provide the irrigation system as defined above, wherein said fluid is selected from oxygen; anesthetic gas for use as local anesthesia, regional anesthesia and general anesthesia selected from ethers, halogenated ethers, desflurane (2,2,2-trifluoro-1-fluoroethyl-difluoromethyl ether, sevoflurane (2,2,2-trifluoro-1-[trifluoromethyl]ethyl fluoromethyl ether), and isoflurane (2-chloro-2-(difluoromethoxy)-1,1,1-trifluoro-ethane); blood; saline; glycine; water; plasma; medicament and any combination thereof.

It is another object of the present invention to provide the irrigation system as defined above, wherein said system is adapted to deliver several substantially different fluids.

It is another object of the present invention to provide the irrigation system as defined above, wherein said substantially different fluids are provided to said patient in substantially the same amounts, in different amounts, at substantially the same rates, at different rates, and any combination thereof.

It is another object of the present invention to provide the irrigation system as defined above, wherein said fluid transfer system comprises at least at least two fluid transfer heads.

It is another object of the present invention to provide the irrigation system as defined above, wherein said at least one fluid transfer head comprises at least one internal reservoir for accommodating said fluid and for delivering said fluid while said fluid transfer head linearly moves along said main longitudinal axis.

It is another object of the present invention to provide the irrigation system as defined above, wherein said at least one fluid transfer head comprises at least one internal reservoir for accommodating said fluid and for delivering said fluid while said fluid transfer head radially moves around said main longitudinal axis.

It is another object of the present invention to provide the irrigation system as defined above, wherein said reservoir system comprises:

a plurality of N support shelves adapted to support each of said containers of said fluid;

support means adapted to support said shelves and to maintain a predetermined distance and orientation between pairs of shelves; and, a plurality of at least N slots in said shelf support means, said slots positioned such that at least one slot is located proximate to each of said N shelves.

It is another object of the present invention to provide the irrigation system as defined above, wherein said support is selected from a group consisting of shelf, drawer, receptacle, sliding receptacle and any combination thereof.

It is another object of the present invention to provide the irrigation system as defined above, wherein said containers are bags made of a flexible material.

It is another object of the present invention to provide the irrigation system as defined above, wherein said containers are made of a rigid material.

It is another object of the present invention to provide the irrigation system as defined above, wherein said rigid material is glass, plastic, ceramic, metal, and any combination thereof.

It is another object of the present invention to provide the irrigation system as defined above, wherein said reservoir system further comprising monitoring means adapted to constantly monitor at least one of the group consisting of the amount of fluid extracted from said reservoir system, the amount of fluid remained in said reservoir system and any combination thereof and reporting means adapted to report the value of said at least one determination.

It is another object of the present invention to provide the irrigation system as defined above, wherein said reservoir system further comprises weight measuring and reporting means adapted to determine the weight of each of said containers and to report the value of said determination.

It is another object of the present invention to provide the irrigation system as defined above, wherein said reservoir system further comprises volume measuring and reporting means adapted to determine the volume of each of said containers and to report the value of said determination.

It is another object of the present invention to provide the irrigation system as defined above, wherein said reservoir system further comprises at least one image sensor adapted to provide real time images of each of said containers.

It is another object of the present invention to provide the irrigation system as defined above, wherein said image sensor is selected from a group consisting of a camera, a video and any combination thereof.

It is another object of the present invention to provide the irrigation system as defined above, wherein said reservoir system further comprises at least one processing unit in communication with said at least one image sensor, adapted for real time image processing of said images such that either the volume or the weight of each of said containers is provided.

It is another object of the present invention to provide the irrigation system as defined above, wherein said reporting means is in communication with said control means.

It is another object of the present invention to provide the irrigation system as defined above, further comprising support rotation means adapted to allow rotation of each of said supports about an axis parallel to its longitudinal axis, said support rotation means further adapted to allow each of said supports to be fixed at an angle chosen by the operator of said irrigation system; said angle is adapted to be fixed prior to said irrigation, during said irrigation and any combination thereof.

It is another object of the present invention to provide the irrigation system as defined above, wherein said angle is in a range of about 0 degrees to about 90 degrees.

It is another object of the present invention to provide the irrigation system as defined above, wherein each of said containers comprises a neck and a nipple, and further wherein said irrigation system further comprises at least one connector between said container and said fluid transfer head, wherein said connector is reversibly coupled to said irrigation system and comprises:
  a lower section comprising two arcs, the first of which is of a diameter and depth adapted to support said neck, and the second of which is of a diameter and depth adapted to support said nipple, the distance between the centers of said arcs substantially equal to the distance between the centers of said neck and said nipple; and,
  an upper section hingedly connected to said lower section, said upper section comprising two arcs of diameters substantially identical to those of the corresponding arcs of said lower section, said two arcs disposed such that closure of said hinged connection forms at least one circular hollow passageway passing through said connector.

It is another object of the present invention to provide the irrigation system as defined above, wherein said system additionally comprising means adapted to fix said containers in place, to verify said containers are in place and any combination thereof.

It is another object of the present invention to provide the irrigation system as defined above, wherein said fluid transfer system further comprises fluid transfer head support means adapted to support said fluid transfer heads; said fluid transfer head support means adapted to allow vertical motion, radial motion and any combination thereof of at least one of said fluid transfer heads.

It is another object of the present invention to provide the irrigation system as defined above, wherein each of said fluid transfer heads comprises
  a spike;
  flexible tubing in fluid contact with said spike;
  ejecting and retracting means for ejecting at least one of said spike and said fluid transfer head a predetermined minimum distance along the horizontal axis from a resting position to an ejected position and for retracting said at least one of said spike and said fluid transfer head from said ejected position to said resting position;
  height fixing means adapted to fix the vertical position of said fluid transfer head.

It is another object of the present invention to provide the irrigation system as defined above, wherein said flexible tubing further comprises at least one internal reservoir for accommodating said fluid and for delivering said fluid while said fluid transfer head linearly moves along said main longitudinal axis.

It is another object of the present invention to provide the irrigation system as defined above, wherein said flexible tubing further comprises at least one internal reservoir for accommodating said fluid and for delivering said fluid while said fluid transfer head radially moves around said main longitudinal axis.

It is another object of the present invention to provide the irrigation system as defined above, wherein said system additionally comprising height fixing means adapted to fix the vertical position of said fluid transfer head or heads along said main longitudinal axis of said reservoir system.

It is another object of the present invention to provide the irrigation system as defined above, wherein at least one of said fluid transfer heads further comprises an actuator in mechanical contact with said fluid transfer head support means and in electronic connection with said control means, said actuator adapted to engage with said fluid transfer head support means, whereby actuation of said actuator by a command from said control means causes vertical motion of said fluid transfer head along the vertical axis of said fluid transfer support means through a distance determined by said control means.

It is another object of the present invention to provide the irrigation system as defined above, wherein said actuator comprises at least one selected from a group consisting of stepper motor, voice command actuator, motion detector and any combination thereof.

It is another object of the present invention to provide the irrigation system as defined above, wherein said fluid regulating means comprises:
  pressure applying means mounted proximate to said flexible tubing in fluid contact with said spike; and,
  extending and retracting means in mechanical contact with said pressure applying means, said extending and retracting means adapted to reversibly extend said pressure applying means.

It is another object of the present invention to provide the irrigation system as defined above, wherein said fluid regulating means is adapted to activate or de-activate fluid flow in said irrigation system.

It is another object of the present invention to provide the irrigation system as defined above, wherein said extending and retracting means comprise a retractable spring.

It is another object of the present invention to provide the irrigation system as defined above, wherein said extending and retracting means are actuated by a means chosen from the group consisting of manual means, mechanical means, electrical means, pneumatic means, electromechanical means, electropneumatic means and any combination thereof.

It is another object of the present invention to provide the irrigation system as defined above, wherein said fluid regulating means comprises at least one selected from a group consisting of a pinch valve, a wheel-like shaped element adapted to apply pressure, and any combination thereof.

It is another object of the present invention to provide the irrigation system as defined above, wherein said pumping system comprises a peristaltic pump.

It is another object of the present invention to provide the irrigation system as defined above, wherein said pumping system comprises a single inlet, and further wherein at least two of said containers are in fluid connection with said single inlet.

It is another object of the present invention to provide the irrigation system as defined above, wherein two of said containers are in fluid connection with a "Y" joint located downstream of said fluid transfer heads.

It is another object of the present invention to provide the irrigation system as defined above, wherein said control system comprises a computer in communication with at least one of said reservoir system, said fluid transfer system, and said pumping system, and further wherein said control system is adapted to direct the flow of fluid through said system.

It is another object of the present invention to provide the irrigation system as defined above, wherein said system further comprising:
  at least one additional container in fluid connection with said pumping means;
  means for opening and closing said fluid connection; and,
  a rack adapted to hang said additional containers.

It is another object of the present invention to provide the irrigation system as defined above, wherein said system further comprising an emergency shutoff switch adapted to halt flow of fluid through said irrigation system.

It is another object of the present invention to provide the irrigation system as defined above, wherein said control system is adapted to prevent over pressure of said fluid in said irrigation system.

It is another object of the present invention to provide the irrigation system as defined above, wherein said over pressure is prevented by means of at least one pressure sensor located in said pumping system.

It is another object of the present invention to provide the irrigation system as defined above, wherein said over pressure is prevented by means of at least one pressure sensor in communication with said outer tubing system.

It is another object of the present invention to provide the irrigation system as defined above, wherein said over pressure is prevented by means of at least one pressure sensor located within said outer tubing system.

It is another object of the present invention to provide the irrigation system as defined above, wherein said over pressure is prevented by means of at least one pressure sensor surrounding at least a portion of said outer tubing system.

It is another object of the present invention to provide the irrigation system as defined above, wherein said over pressure is prevented by means of limiting the pumping system to predetermined values.

It is another object of the present invention to provide the irrigation system as defined above, wherein said system further comprises removing means for removing a protective cover or cap from said container.

It is another object of the present invention to provide the irrigation system as defined above, wherein said system additionally comprising at least one holder, said at least one holder enabled to contain caps and covers removed from none or more of a group consisting of fluid containers, spikes, and fluid transfer heads during operation of said system.

It is another object of the present invention to provide the irrigation system as defined above, wherein said removing means comprise cutting means and actuating means adapted to actuate said cutting means.

It is another object of the present invention to provide the irrigation system as defined above, wherein said removing means comprise pressure applying means, adapted to apply pressure on said cover or cap by at least one of a group consisting of pulling, pushing, and twisting said cover or cap.

It is another object of the present invention to provide the irrigation system as defined above, additionally comprising at least one holder, said at least one holder enabled to contain caps and covers removed from none or more of a group consisting of fluid containers, spikes, and fluid transfer heads during operation of said system.

It is another object of the present invention to provide the irrigation system as defined above, wherein said fluid transfer head additionally comprises a connector, said connector configured such that said spike can not be coupled to said fluid transfer head before removal of protective covers from said spike.

It is another object of the present invention to provide the irrigation system as defined above, wherein said system is enabled to provide continuous and controlled flow of a fluid to a plurality of patients.

It is another object of the present invention to provide the irrigation system as defined above, wherein said system is enabled to provide continuous and controlled flow of a plurality of fluids to a plurality of patients.

It is another object of the present invention to provide a method for providing a substantially continuous and controlled flow of a fluid from a reservoir that comprises plurality of N containers, each of said N containers at a predetermined height and location, wherein said method comprises:
  a. obtaining fluid extracting means;
  b. obtaining at least two fluid transfer heads, each of said fluid transfer heads comprising:
    a spike;
    flexible tubing in fluid contact with said spike;
    ejecting and retracting means for ejecting at least one of said spike and said fluid transfer head a predetermined minimum distance from a resting position to an ejected position and for retracting said at least one of said spike and said fluid transfer head from said ejected position to said resting position;
    a fluid exit in fluid contact with said flexible tubing; and,
    height fixing means adapted to fix the vertical position of said fluid transfer head;
  c. placing a first fluid transfer head proximate to a first container from which pumping has not yet commenced;
  d. placing a second fluid transfer head proximate to a second container from which pumping has not yet commenced;

e. connecting the fluid exits of said fluid transfer heads to a single outlet, and to said pumping means;
f. fixing the height of said second fluid transfer head to the height of said second container from which pumping has not yet commenced, such that upon ejection of the spike, the wall of said second container will be pierced;
g. using said fluid regulating means to block flow of fluid from said first fluid transfer head;
h. using said fluid regulating means to block flow of fluid from said second fluid transfer head;
i. removing protective cover of said first container;
j. ejecting said spike of said first fluid transfer head, thereby creating a fluid connection between the interior of said first container and said single outlet;
k. removing protective cover of said second container;
l. ejecting said spike of said second fluid transfer head, thereby creating a fluid connection between the interior of said second container and said single outlet;
m. using said fluid regulating means to permit flow of fluid from said first fluid transfer head;
n. actuating said pumping means;
o. extracting said fluid from said first container until the fluid level in said first container is reduced to a predetermined quantity;
p. using said fluid regulating means to permit flow of fluid from said second fluid transfer head;
q. using said fluid regulating means to block flow of fluid from said first fluid transfer head;
r. extracting said fluid from said second container until the fluid level in said second container is reduced to a predetermined quantity;
s. using said fluid regulating means to permit flow of fluid from said first fluid transfer head;
t. using said fluid regulating means to block flow of fluid from said second fluid transfer head;
u. retracting said spike into said second fluid transfer head;
v. placing said second fluid transfer head proximate to another container from which pumping has not yet commenced;
w. fixing the height of said second fluid transfer head to the height of said another container, such that upon ejection of the spike, the wall of said another container will be pierced;
x. removing protective cover of said another container;
y. ejecting said spike of said second fluid transfer head, thereby creating a fluid connection between the interior of said another container and said single outlet;
z. using said fluid regulating means to permit flow of fluid from said second fluid transfer head;
za. using said fluid regulating means to block flow of fluid from said first fluid transfer head;
zb. extracting said fluid from said another container until the fluid level in said another container is reduced to a predetermined quantity;
repeating sequentially, for each of the remaining containers, said steps of s-zb.

It is another object of the present invention to provide a method for providing a substantially continuous and controlled flow of a fluid from a reservoir that comprises plurality of N containers, each of said N containers at a predetermined height and location, wherein said method comprises:
a. obtaining fluid extracting means;
b. obtaining at least two fluid transfer heads, each of said fluid transfer heads comprising:
 a spike;
 flexible tubing in fluid contact with said spike;
 ejecting and retracting means for ejecting at least one of said spike and said fluid transfer head a predetermined minimum distance from a resting position to an ejected position and for retracting said at least one of said spike and said fluid transfer head from said ejected position to said resting position;
 a fluid exit in fluid contact with said flexible tubing; and,
 height fixing means adapted to fix the vertical positions of said fluid transfer heads;
c. placing a first fluid transfer head proximate to a first container from which pumping has not yet commenced;
d. placing a second fluid transfer head proximate to a second container from which pumping has not yet commenced;
e. connecting the fluid exits of said fluid transfer heads to a single outlet;
f. fixing the height of said second fluid transfer head to the height of said second container, such that upon ejection of the spike, the wall of said second container will be pierced;
g. using said fluid regulating means to block flow of fluid from said first fluid transfer head;
h. using said fluid regulating means to block flow of fluid from said second fluid transfer head;
i. removing protective cover of said first container;
j. ejecting said spike of said first fluid transfer head, thereby creating a fluid connection between the interior of said first container and said single outlet;
k. removing protective cover of the second container;
l. ejecting said spike of said second fluid transfer head, thereby creating a fluid connection between the interior of said second container and said single outlet;
m. applying pressure on said first container so as to extract fluid from the same;
n. using said fluid regulating means to permit flow of fluid from said first fluid transfer head;
o. extracting said fluid from said first container until the fluid level in said first container is reduced to a predetermined quantity;
p. applying pressure on said second container so as to extract fluid from the same;
q. using said fluid regulating means to permit flow of fluid from said second fluid transfer head;
r. using said fluid regulating means to block flow of fluid from said first fluid transfer head;
s. discontinuing applying pressure on said first container;
t. extracting said fluid from said second container until the fluid level in said second container is reduced to a predetermined quantity;
u. applying pressure on said first container so as to extract fluid from the same;
v. using said fluid regulating means to permit flow of fluid from said first fluid transfer head;
w. using said fluid regulating means to block flow of fluid from said second fluid transfer head;
x. discontinuing applying pressure on said second container;
y. retracting said spike into said second fluid transfer head;
z. placing said second fluid transfer head proximate to another container from which pumping has not yet commenced;
za. fixing the height of said second fluid transfer head to the height of said another container, such that upon ejection of the spike, the wall of said another container will be pierced;
zb. removing protective cover of said another container;

zc. ejecting said spike of said second fluid transfer head, thereby creating a fluid connection between the interior of said another container and said single outlet;

zd. applying pressure on said another container so as to extract fluid from the same;

ze. using said fluid regulating means to permit flow of fluid from said second fluid transfer head;

zf. using said fluid regulating means to block flow of fluid from said first fluid transfer head;

zg. discontinuing applying pressure on said first container;

zh. extracting said fluid from said another container until the fluid level in said another container is reduced to a predetermined quantity;

repeating sequentially, for each of the remaining containers, said steps of u-zh.

It is another object of the present invention to provide a method for providing a substantially continuous and controlled flow of a fluid from a reservoir that comprises plurality of N containers, each of said N containers at a predetermined height and location, wherein said method comprises:

a. obtaining fluid extracting means;

b. obtaining at least two fluid transfer heads, each of said fluid transfer heads comprising:
a spike;
flexible tubing in fluid contact with said spike;
ejecting and retracting means for ejecting at least one of said spike and said fluid transfer head a predetermined minimum distance from a resting position to an ejected position and for retracting said at least one of said spike and said fluid transfer head from said ejected position to said resting position;
a fluid exit in fluid contact with said flexible tubing; and,
height fixing means adapted to fix the vertical position of said fluid transfer head;

c. placing a first fluid transfer head proximate to a first container from which pumping has not yet commenced;

d. placing a second fluid transfer head proximate to a second container from which pumping has not yet commenced;

e. connecting the fluid exits of said fluid transfer heads to a single outlet, and to said pumping means;

f. fixing the height of said first fluid transfer head to the height of said first container, such that upon ejection of the spike, the wall of said first container will be pierced;

g. fixing the height of said second fluid transfer head to the height of said second container, such that upon ejection of the spike, the wall of said second container will be pierced;

h. using said fluid regulating means to block flow of fluid from said first fluid transfer head;

i. using said fluid regulating means to block flow of fluid from said second fluid transfer head;

j. removing protective cover of said first container;

k. ejecting said spike of said first fluid transfer head, thereby creating a fluid connection between the interior of said first container and said single outlet;

l. removing protective cover of the second container;

m. ejecting said spike of said second fluid transfer head, thereby creating a fluid connection between the interior of said second container and said single outlet;

n. using said fluid regulating means to permit flow of fluid from said first fluid transfer head;

o. actuating said pumping means;

p. extracting said fluid from said first container until the fluid level in said first container is reduced to a predetermined quantity;

q. using said fluid regulating means to permit flow of fluid from said second fluid transfer head;

r. using said fluid regulating means to block flow of fluid from said first fluid transfer head;

s. extracting said fluid from said second container until the fluid level in said second container is reduced to a predetermined quantity;

t. retracting said spike into said first fluid transfer head;

u. placing said first fluid transfer head proximate to another available container;

v. fixing the height of said first fluid transfer head to the height of said said another container, such that upon ejection of the spike, the wall of said another container will be pierced;

w. removing protective cover of said another container;

x. ejecting said spike of said first fluid transfer head, thereby creating a fluid connection between the interior of said another container and said single outlet;

y. using said fluid regulating means to permit flow of fluid from said first fluid transfer head;

z. using said fluid regulating means to block flow of fluid from said second fluid transfer head;

za. extracting said fluid from said another container until the fluid level in said another container is reduced to a predetermined quantity zb. retracting said spike into said second fluid transfer head;

zc. placing said second fluid transfer head proximate to another available container;

zd. fixing the height of said second fluid transfer head to the height of said said another container, such that upon ejection of the spike, the wall of said another container will be pierced;

ze. removing protective cover of said another container;

zf. ejecting said spike of said second fluid transfer head, thereby creating a fluid connection between the interior of said another container and said single outlet;

zg. using said fluid regulating means to permit flow of fluid from said second fluid transfer head;

zh. using said fluid regulating means to block flow of fluid from said first fluid transfer head;

zi. extracting said fluid from said another container until the fluid level in said another container is reduced to a predetermined quantity repeating sequentially, for each of the remaining available containers and respective fluid transfer head, said steps of t-zi.

It is another object of the present invention to a method for providing a substantially continuous and controlled flow of a fluid from a reservoir that comprises plurality of N containers, each of said N containers at a predetermined height and location, wherein said method comprises:

a. obtaining fluid extracting means;

b. obtaining at least two fluid transfer heads, each of said fluid transfer heads comprising:
a spike;
flexible tubing in fluid contact with said spike;
ejecting and retracting means for ejecting at least one of said spike and said fluid transfer head a predetermined minimum distance from a resting position to an ejected position and for retracting said at least one of said spike and said fluid transfer head from said ejected position to said resting position;
a fluid exit in fluid contact with said flexible tubing; and,
height fixing means adapted to fix the vertical position of said fluid transfer head;

c. placing a first fluid transfer head proximate to a first container from which pumping has not yet commenced;
d. placing a second fluid transfer head proximate to a second container from which pumping has not yet commenced;
e. connecting the fluid exits of said fluid transfer heads to a single outlet;
f. fixing the height of said first fluid transfer head to the height of said first container, such that upon ejection of the spike, the wall of said first container will be pierced;
g. fixing the height of said second fluid transfer head to the height of said second container, such that upon ejection of the spike, the wall of said second container will be pierced;
h. using said fluid regulating means to block flow of fluid from said first fluid transfer head;
i. using said fluid regulating means to block flow of fluid from said second fluid transfer head;
j. removing protective cover of said first container;
k. ejecting said spike of said first fluid transfer head, thereby creating a fluid connection between the interior of said first container and said single outlet;
l. removing protective cover of the second container;
m. ejecting said spike of said second fluid transfer head, thereby creating a fluid connection between the interior of said second container and said single outlet;
n. applying pressure on said first container so as to extract fluid from the same;
o. using said fluid regulating means to permit flow of fluid from said first fluid transfer head;
p. extracting said fluid from said first container until the fluid level in said first container is reduced to a predetermined quantity;
q. applying pressure on said second container so as to extract fluid from the same;
r. using said fluid regulating means to permit flow of fluid from said second fluid transfer head;
s. using said fluid regulating means to block flow of fluid from said first fluid transfer head;
t. discontinuing applying pressure on said first container;
u. extracting said fluid from said second container until the fluid level in said second container is reduced to a predetermined quantity;
v. retracting said spike into said first fluid transfer head;
w. placing said first fluid transfer head proximate to another available container;
x. fixing the height of said first fluid transfer head to the height of said another container, such that upon ejection of the spike, the wall of said another container will be pierced;
y. removing protective cover of said another container;
z. ejecting said spike of said first fluid transfer head, thereby creating a fluid connection between the interior of said another container and said single outlet;
za. applying pressure on said another container so as to extract fluid from the same;
zb. using said fluid regulating means to permit flow of fluid from said first fluid transfer head;
zc. using said fluid regulating means to block flow of fluid from said second fluid transfer head;
zd. discontinuing applying pressure on said second container;
ze. extracting said fluid from said another container until the fluid level in said another container is reduced to a predetermined quantity;
zf. retracting said spike into said second fluid transfer head;
zg. placing said second fluid transfer head proximate to yet another container from which pumping has not yet commenced;
zh. fixing the height of said second fluid transfer head to the height of said yet another container, such that upon ejection of the spike, the wall of said yet another container will be pierced;
zi. removing protective cover of said yet another container;
zg. ejecting said spike of said second fluid transfer head, thereby creating a fluid connection between the interior of said yet another container and said single outlet;
zk. applying pressure on said another container so as to extract fluid from the same;
zl. using said fluid regulating means to permit flow of fluid from said second fluid transfer head;
zm. using said fluid regulating means to block flow of fluid from said first fluid transfer head;
zn. discontinuing applying pressure on said yet another container from first fluid transfer head;
zo. extracting said fluid from said yet another container until the fluid level in said yet another container is reduced to a predetermined quantity repeating sequentially, for each of the remaining available containers and respective fluid transfer head, said steps of t-zo.

It is another object of the present invention to provide a method for providing a substantially continuous and controlled flow of a fluid from a reservoir that comprises plurality of N containers, each of said N containers at a predetermined height and location, wherein said method comprises:
  a. obtaining fluid extracting means;
  b. obtaining at least one fluid transfer head, said at least one fluid transfer head comprising:
    a spike;
    flexible tubing in fluid contact with said spike;
    an internal reservoir for accommodating said fluid and for delivering said fluid in fluid contact with said flexible tubing;
    ejecting and retracting means for ejecting at least one of said spike and said fluid transfer head a predetermined minimum distance from a resting position to an ejected position and for retracting said at least one of said spike and said fluid transfer head from said ejected position to said resting position;
    a fluid exit in fluid contact with said flexible tubing; and,
    height fixing means adapted to fix the vertical position of said fluid transfer head;
  c. placing said fluid transfer head proximate to a first container from which pumping has not yet commenced;
  d. connecting the fluid exits of said fluid transfer beads to said pumping means;
  e. fixing the height of said fluid transfer head to the height of said first container, such that upon ejection of the spike, the wall of said first container will be pierced;
  f. using said fluid regulating means to block flow of fluid from said fluid transfer head;
  g. removing protective cover of said first container;
  h. ejecting said spike of said fluid transfer head, thereby creating a fluid connection between the interior of said first container and said single outlet;
  i. using said fluid regulating means to permit flow of fluid from said fluid transfer head;
  j. actuating said pumping means;
  k. filling said internal reservoir with said fluid;
  l. extracting said fluid from said first container until the fluid level in said first container is reduced to a predetermined quantity;

m. using said fluid regulating means to block flow of fluid from said fluid transfer head;
n. extracting said fluid from the said internal reservoir;
o. retracting said spike into said fluid transfer head;
p. placing said fluid transfer head proximate to another container from which pumping has not yet commenced;
q. fixing the height of said fluid transfer head to the height of said another container, such that upon ejection of the spike, the wall of said another container will be pierced;
r. removing protective cover of said another container;
s. ejecting said spike of said fluid transfer head, thereby creating a fluid connection between the interior of said another container and said single outlet;
t. using said fluid regulating means to permit flow of fluid from said another fluid transfer head;
u. filling said internal reservoir with said fluid;
v. extracting said fluid from said container until the fluid level in said another container is reduced to a predetermined quantity;
repeating sequentially, for each of the remaining available containers, said steps of m-v.

It is another object of the present invention to provide a method for providing a substantially continuous and controlled flow of a fluid from a reservoir that comprises plurality of N containers, each of said N containers at a predetermined height and location, wherein said method comprises:
a. obtaining fluid extracting means;
b. obtaining at least one fluid transfer head, said fluid transfer head comprising:
a spike;
flexible tubing in fluid contact with said spike;
an internal reservoir for accommodating said fluid and for delivering said fluid in fluid contact with said flexible tubing;
ejecting and retracting means for ejecting at least one of said spike and said fluid transfer head a predetermined minimum distance from a resting position to an ejected position and for retracting said at least one of said spike and said fluid transfer head from said ejected position to said resting position;
a fluid exit in fluid contact with said flexible tubing; and,
height fixing means adapted to fix the vertical position of said fluid transfer head;
c. placing said fluid transfer head proximate to a first container from which pumping has not yet commenced;
d. fixing the height of said fluid transfer head to the height of said first container, such that upon ejection of the spike, the wall of said first container will be pierced;
e. using said fluid regulating means to block flow of fluid from said fluid transfer head;
f. removing protective cover of said first container;
g. ejecting said spike of said fluid transfer head, thereby creating a fluid connection between the interior of said first container and said single outlet;
h. applying pressure on said first container so as to extract fluid from the same;
i. using said fluid regulating means to permit flow of fluid from said fluid transfer head;
j. filling said internal reservoir with said fluid;
k. extracting said fluid from said first container until the fluid level in said first container is reduced to a predetermined quantity;
l. using said fluid regulating means to block flow of fluid from said fluid transfer head;
m. discontinuing applying pressure on said first container from first fluid transfer head;
n. extracting said fluid from the said internal reservoir;
o. retracting said spike into said fluid transfer head;
p. placing said fluid transfer head proximate to another container from which pumping has not yet commenced;
q. fixing the height of said fluid transfer head to the height of said another container, such that upon ejection of the spike, the wall of said another container will be pierced;
r. removing protective cover of said another container;
s. ejecting said spike of said fluid transfer head, thereby creating a fluid connection between the interior of said another container and said single outlet;
t. applying pressure on said another container so as to extract fluid from the same;
u. using said fluid regulating means to permit flow of fluid from said another fluid transfer head;
v. filling said internal reservoir with said fluid;
w. extracting said fluid from said container until the fluid level in said another container is reduced to a predetermined quantity;
repeating sequentially, for each of the remaining available containers, said steps of l-w.

It is another object of the present invention to provide the method as defined above, additionally comprising a step of removing at least one of the containers' caps.

It is another object of the present invention to provide the method as defined above, wherein said system additionally comprising a step of extracting said fluid simultaneously from at least two of said containers.

It is another object of the present invention to provide the method as defined above, wherein said system additionally comprising a step of extracting said fluid simultaneously from at least two of said containers, further wherein none or more of the group consisting of pressure on said containers and the flow rate from said containers differ between any two of said at least two containers.

It is another object of the present invention to provide the method as defined above, wherein said fluid extracting means are selected from a group consisting of pumping means for withdrawing fluid out of said container, pressure applying means adapted to apply pressure on said container such that fluid is extracted from the same, and any combination thereof.

It is another object of the present invention to provide the method as defined above, wherein said step of extracting said fluid comprises either (a) pumping said fluid from said container; (b) applying pressure on said container such that fluid is extracted from the same; and any combination thereof.

It is another object of the present invention to provide the method as defined above, wherein said pressure applying means are selected from a group consisting of a membrane encapsulating at least one of said containers of fluid, squeezing means adapted to apply squeezing pressure on at least one of said containers and any combination thereof.

It is another object of the present invention to provide the method as defined above, wherein said squeezing means are selected from pneumatic compression of at least one of the containers, hydrostatic compression of at least one of the containers, and any combination thereof.

It is another object of the present invention to provide the method as defined above, wherein said system further comprising a step of using said fluid regulating means to block flow of fluid from said first container at any time that flow is permitted from another container.

It is another object of the present invention to provide the method as defined above, wherein said system further comprising a step of determining the weight of each of said of said containers in order to determine the level of fluid within.

It is another object of the present invention to provide the method as defined above, wherein said system further comprising a step of notifying the user upon the occurrence of at least one condition chosen from the group consisting of (a) the beginning of pumping of fluid from the Nth of said N containers; (b) a failure of a predetermined component; (c) a drop in the rate of flow of fluid below a predetermined threshold; (d) a drop in the level of fluid in a predetermined container of said N containers below a predetermined threshold; (e) time from the beginning of the procedure; (f) number of containers being used.

It is another object of the present invention to provide the method as defined above, wherein said system further comprising steps of:
  ejecting said spike of said first fluid transfer head, thereby creating a fluid connection between said first container and said outlet; and,
  extracting fluid from said first container until the level of fluid within said first container drops by a predetermined amount, by either pumping said fluid or applying pressure on the same so as to extract fluid;
wherein said additional steps are performed after the level of fluid in said other container drops to said predetermined value and before the commencement of pumping of fluid from the following container.

It is another object of the present invention to provide the method as defined above, wherein said system further comprising steps of:
  fixing the height of said first fluid transfer head to the height of another container from which pumping has not yet commenced;
  ejecting said spike of said first fluid transfer head, thereby creating a fluid connection between the interior of said another container and said single outlet;
  either pumping fluid or applying pressure on said another container until the amount of fluid within said another container drops by a predetermined amount; and,
  repeating sequentially steps of fixing the height of each fluid transfer head to the height of a container from which pumping has not yet commenced, ejecting the spike therefrom, and pumping fluid from the current container for each of said fluid transfer heads until the level of fluid within each of said containers has dropped by a predetermined amount.

It is another object of the present invention to provide the method as defined above, wherein said system additionally comprising at least one step of (a) controlling the rate of flow of fluid through said irrigation system according to a predetermined protocol; (b) controlling the movement of said at least one fluid transfer head; (c) controlling the activation of the same; and any combination thereof.

It is another object of the present invention to provide the method as defined above, wherein said system additionally comprising step of withdrawing said fluid from at least one of said containers of fluid in a predetermined rate of flow to an outer tubing system.

It is another object of the present invention to provide the method as defined above, wherein said containers are disposed is a predetermined configuration.

It is another object of the present invention to provide the method as defined above, wherein said predetermined configuration is selected from a group consisting of linear shape, radial shape, ellipsoidal shape, square shape, triangular shape, hexagonal shape, pentagonal shape, any 2D shape, any 3D shape and any combination thereof.

It is another object of the present invention to provide the method as defined above, wherein said system additionally comprising step of regulating at least one of the rate of transfer of fluid from said reservoir system to each of said fluid transfer heads and the pressure at which said fluid is transferred from said reservoir system to each of said fluid transfer heads.

It is another object of the present invention to provide the method as defined above, wherein said system additionally comprising at least one step of (a) controlling the rate of flow of fluid through said irrigation system according to a predetermined protocol; (b) controlling the movement of said at least one fluid transfer head; (c) controlling the activation of the same.

It is another object of the present invention to provide the method as defined above, wherein said system additionally comprising step of selecting said fluid from a group consisting of gas, liquid and any combination thereof.

It is another object of the present invention to provide the method as defined above, wherein said system additionally comprising step of selecting said fluid from oxygen; anesthetic gas for use as local anesthesia, regional anesthesia and general anesthesia selected from ethers, halogenated ethers, desflurane (2,2,2-trifluoro-1-fluoroethyl-difluoromethyl ether, sevoflurane (2,2,2-trifluoro-1-[trifluoromethyl]ethyl fluoromethyl ether), and isoflurane (2-chloro-2-(difluoromethoxy)-1,1,1-trifluoro-ethane); blood; saline; glycine; water; plasma; medicament and any combination thereof.

It is another object of the present invention to provide the irrigation system as defined above, wherein said system is adapted to deliver several substantially different fluids.

It is another object of the present invention to provide the irrigation system as defined above, wherein said substantially different fluids are provided to said patient in substantially the same amounts, different amounts, substantially the same rates, different rates, and any combination thereof.

It is another object of the present invention to provide the method as defined above, additionally comprising a step of providing said reservoir system with:
  a plurality of N support shelves adapted to support each of said containers of said fluid;
  support means adapted to support said shelves and to maintain a predetermined distance and orientation between pairs of shelves; and,
  a plurality of at least N slots in said shelf support means, said slots positioned such that at least one slot is located proximate to each of said N shelves.

It is another object of the present invention to provide the method as defined above, wherein said support is selected from a group consisting of a shelf, a drawer, a receptacle, a sliding receptacle and any combination thereof.

It is another object of the present invention to provide the method as defined above, wherein said system additionally comprising step of providing said containers as bags made of a flexible material.

It is another object of the present invention to provide the method as defined above, wherein said system additionally comprising step of providing said containers as bags made of a rigid material.

It is another object of the present invention to provide the method as defined above, wherein said rigid material is plastic, ceramic, metal, and any combination thereof.

It is another object of the present invention to provide the method as defined above, wherein said system additionally comprising step of constantly monitoring the amount of fluid extracted from said reservoir system and reporting the value of said determination.

It is another object of the present invention to provide the method as defined above, wherein said system additionally comprising step of providing said irrigation system with weight measuring and reporting means adapted to determine the weight of each of said containers and to report the value of said determination.

It is another object of the present invention to provide the method as defined above, wherein said system additionally comprising step of providing said irrigation system with volume measuring and reporting means adapted to determine the volume of each of said containers and to report the value of said determination.

It is another object of the present invention to provide the method as defined above, wherein said system additionally comprising step of providing said irrigation system with at least one image sensor adapted to provide real time images of each of said containers.

It is another object of the present invention to provide the method as defined above, wherein said system additionally comprising step of selecting said image sensor from a group consisting of a camera, a video and any combination thereof.

It is another object of the present invention to provide the method as defined above, wherein said system additionally comprising step of providing said irrigation system with at least one processing unit in communication with said at least one image sensor, adapted for real time image processing of said image such that either the volume or the weight of each of said containers is provided.

It is another object of the present invention to provide the method as defined above, wherein said system additionally comprising step of allowing rotation of each of said supports about an axis parallel to its longitudinal axis, said support rotation means further adapted to allow each of said supports to be fixed at an angle chosen by the operator of said irrigation system.

It is another object of the present invention to provide the method as defined above, wherein said system additionally comprising step of selecting said angle is in a range of about 0 degrees to about 90 degrees.

it is another object of the present invention to provide the method as defined above, wherein said system additionally comprising step of providing each of said containers comprises a neck and a nipple, and further wherein said irrigation system further comprises at least one connector between said container and said fluid transfer head, wherein said connector is reversibly coupled to said irrigation system and comprises:
  a lower section comprising two arcs, the first of which is of a diameter and depth adapted to support said neck, and the second of which is of a diameter and depth adapted to support said nipple, the distance between the centers of said arcs substantially equal to the distance between the centers of said neck and said nipple; and,
  an upper section hingedly connected to said lower section, said upper section comprising two arcs of diameters substantially identical to those of the corresponding arcs of said lower section, said two arcs disposed such that closure of said hinged connection forms at least one circular hollow passageway passing through said connector.

It is another object of the present invention to provide the method as defined above, wherein said system additionally comprising means adapted to fix said containers in place, to verify said containers are in place and any combination thereof.

It is another object of the present invention to provide the method as defined above, wherein said system additionally comprising step of providing said fluid transfer system with fluid transfer head support means adapted to support said fluid transfer heads, said fluid transfer head support means adapted to allow vertical motion, radial motion and any combination thereof of at least one of said fluid transfer heads.

It is another object of the present invention to provide the method as defined above, additionally comprising step of providing each of said fluid transfer heads with:
  a spike;
  flexible tubing in fluid contact with said spike;
  ejecting and retracting means for ejecting at least one of said spike and said fluid transfer head a predetermined minimum distance along the horizontal axis from a resting position to an ejected position and for retracting said at least one of said spike and said fluid transfer head from said ejected position to said resting position.
  height fixing means adapted to fix the vertical position of said fluid transfer head.

It is another object of the present invention to provide the irrigation system as defined above, wherein said flexible tubing further comprises at least one internal reservoir for accommodating said fluid and for delivering said fluid while said fluid transfer head linearly moves along said main longitudinal axis.

It is another object of the present invention to provide the irrigation system as defined above, wherein said flexible tubing further comprises at least one internal reservoir for accommodating said fluid and for delivering said fluid while said fluid transfer head radially moves around said main longitudinal axis.

It is another object of the present invention to provide the method as defined above, wherein said system additionally comprising step of height fixing the vertical position of said fluid transfer head along said main longitudinal axis of said reservoir system.

It is another object of the present invention to provide the method as defined above, wherein said system additionally comprising step of providing at least one of said fluid transfer heads with an actuator in mechanical contact with said fluid transfer head support means and in electronic connection with said control means, said actuator adapted to engage with said fluid transfer head support means, whereby actuation of said actuator by a command from said control means causes vertical motion of said fluid transfer head along the vertical axis of said fluid transfer support means through a distance determined by said control means.

It is another object of the present invention to provide the method as defined above, wherein said system additionally comprising step of selecting said actuator from a group consisting of stepper motor, voice command actuator, motion detector and any combination thereof.

It is another object of the present invention to provide the method as defined above, wherein said system additionally comprising step of providing said fluid regulating means with:
  pressure applying means mounted proximate to said flexible tubing in fluid contact with said spike; and,
  extending and retracting means in mechanical contact with said pressure applying means, said extending and retracting means adapted to reversibly extend said pressure applying means.

It is another object of the present invention to provide the method as defined above, wherein said extending and retracting means comprise a retractable spring.

It is another object of the present invention to provide the method as defined above, wherein said extending and retracting means are actuated by a means chosen from the group consisting of manual means, mechanical means, electrical means, pneumatic means, electromechanical means, electropneumatic means and any combination thereof.

It is another object of the present invention to provide the method as defined above, wherein said fluid regulating means comprises at least one selected from a group consisting of a pinch valve, a wheel-like shaped element adapted to apply pressure, and any combination thereof.

It is another object of the present invention to provide the method as defined above, additionally comprising step of selecting said pumping system comprises a peristaltic pump.

It is another object of the present invention to provide the method as defined above, wherein said pumping system comprises a single inlet, and further wherein at least two of said containers are in fluid connection with said single inlet.

It is another object of the present invention to provide the method as defined above, wherein two of said containers are in fluid connection with a "Y" joint located downstream of said fluid transfer heads.

It is another object of the present invention to provide the method as defined above, wherein said system additionally comprising step of providing said irrigation system with:
  at least one additional container in fluid connection with said pumping means;
  means for opening and closing said fluid connection; and,
  a rack adapted to hang said additional containers.

It is another object of the present invention to provide the method as defined above, wherein said system additionally comprising step of providing said irrigation system with an emergency shutoff switch adapted to halt flow of fluid through said irrigation system.

It is another object of the present invention to provide the method as defined above, wherein said system additionally comprising step of preventing over pressure of said fluid in said irrigation system.

It is another object of the present invention to provide the method as defined above, wherein said over pressure is prevented by means of at least one pressure sensor located in said pumping system.

It is another object of the present invention to provide the method as defined above, wherein said over pressure is prevented by means of at least one pressure sensor in communication with said outer tubing system.

It is another object of the present invention to provide the method as defined above, wherein said over pressure is prevented by means of at least one pressure sensor located within said outer tubing system.

It is another object of the present invention to provide the method as defined above, wherein said over pressure is prevented by means of at least one pressure sensor surrounding at least a portion of said outer tubing system.

It is another object of the present invention to provide the method as defined above, wherein said over pressure is prevented by means of pre-setting the maximum pressure to which said pump can reach.

It is another object of the present invention to provide the method as defined above, wherein said system additionally comprising step of providing said irrigation system with removing means for removing a protective cover or cap from said container.

It is another object of the present invention to provide the method as defined above, wherein said system additionally comprising step of providing said irrigation system with an automatic collecting means adapted to collect said cover or cap from said irrigation system.

It is another object of the present invention to provide the method as defined above, wherein said removing means comprise cutting means and actuating means adapted to actuate said cutting means.

It is another object of the present invention to provide the method as defined above, wherein said removing means comprise pressure applying means, adapted to apply pressure on said cover or cap by at least one of a group consisting of pulling, pushing, and twisting said cover or cap.

It is another object of the present invention to provide the method as defined above, additionally comprising step of identifying an empty container.

It is another object of the present invention to provide the method as defined above, additionally comprising step of moving at least one of said fluid transfer head to said empty container.

It is another object of the present invention to provide the method as defined above, wherein said containers are disposed in a predetermined configuration.

It is another object of the present invention to provide the method as defined above, wherein said predetermined configuration is selected from a group consisting of linear configuration, radial configuration, ellipsoidal configuration, square configuration, triangular configuration, hexagonal configuration, pentagonal configuration, any 2D-shaped configuration, any 3D shaped configuration and any combination thereof.

It is another object of the present invention to provide the method as defined above, further including a step of removing a protective cover or cap from said container.

It is another object of the present invention to provide the method as defined above, additionally comprising a step of collecting said cover or cap from said irrigation system.

It is another object of the present invention to provide the method as defined above, additionally comprising a step of providing at least one holder, said at least one holder enabled to contain caps and covers removed from none or more of a group consisting of fluid containers, spikes, and fluid transfer heads during operation of said system.

It is another object of the present invention to provide the method as defined above, wherein said fluid transfer head additionally comprises a connector, said connector configured such that said spike can not be coupled to said fluid transfer head before removal of protective covers from said spike.

It is another object of the present invention to provide the method as defined above, additionally comprising a step of providing said system with tubing and valves such as to enable said system to provide continuous and controlled flow of a fluid to a plurality of patients.

It is another object of the present invention to provide the method as defined above, additionally comprising a step of providing said system with tubing and valves such as to enable said system to provide continuous and controlled flow of a plurality of fluids to a plurality of patients.

BRIEF DESCRIPTION OF THE DRAWINGS

The invention herein disclosed is described with reference to the drawings, in which.

DETAILED DESCRIPTION OF THE PREFERRED EMBODIMENTS

Figure 1:
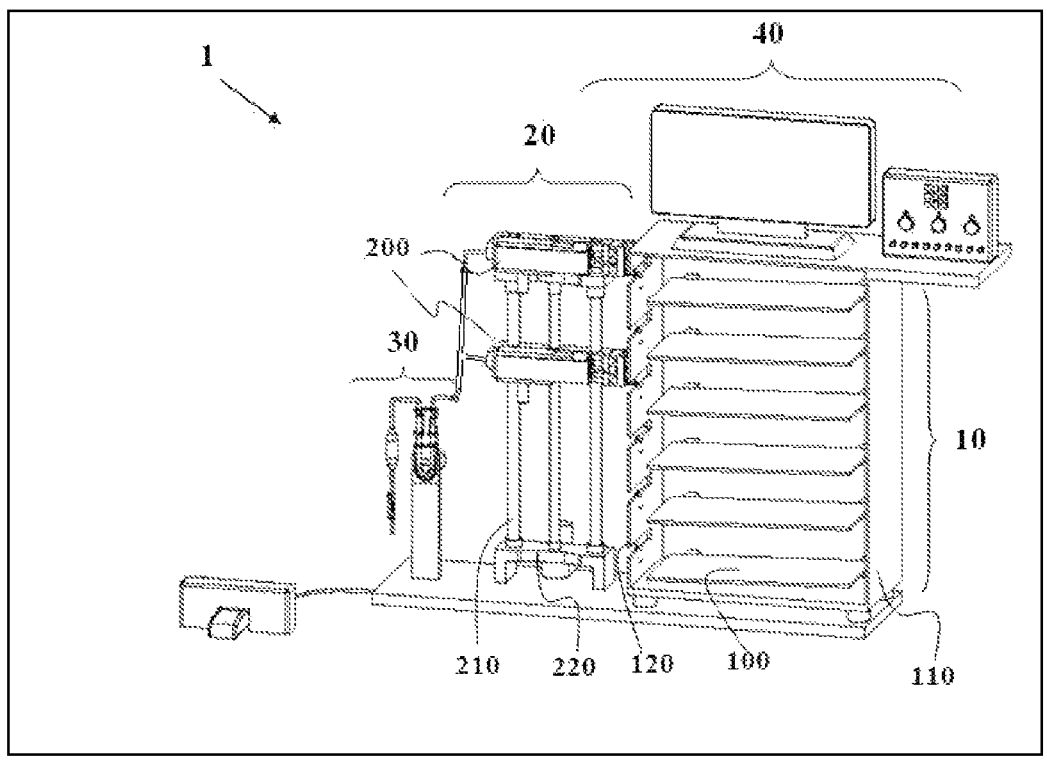
FIG. 1 presents a schematic assembly diagram of the apparatus disclosed herein according to one embodiment of the present invention.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification, but only as indicated in the accompanying claims, with the proper scope determined only by the broadest interpretation of said claims.

The term 'eject' hereinafter refers to extending a spike from a retracted position such that the spike penetrates the wall of a fluid container. After ejection of a spike, there is fluid connection between the interior of the fluid container and the interior of the spike.

The term 'plurality' hereinafter refers to any integer greater than one.

The present invention provides a unique robotic and fully automated solution, based on using solution bags such as those used in prior art with an electro-mechanic machine that automatically replaces switches between containers, thereby obviating the need for a manual change of containers.

The system consists of several sub mechanisms; such as, but not limited to a mechanism that will identify when the bag/container is about to empty (or alternatively, to monitor/identify the amount of fluid within the same), identify an empty/full bag, switch the bag automatically, spike it and build pressure according to the surgeon's needs thus enabling a Continuous Irrigation.

The present invention provides an irrigation system for providing a continuous and controlled flow of a fluid, wherein said system comprises:

(a) a reservoir system comprising a plurality of containers of fluid; said reservoir system is characterized by a main longitudinal axis; (b) a fluid transfer system in fluid connection with said reservoir system, said fluid transfer system comprising: at least one fluid transfer head, adapted to transfer fluid from one of said plurality of reservoirs to an external tubing system; wherein each of said fluid transfer heads is characterized by a mechanism adapted to linearly move each of said fluid transfer heads along said main longitudinal axis.

The present invention further provides an irrigation system for providing a continuous and controlled rate flow of a fluid, wherein said system comprises: (a) a reservoir system comprising a plurality of containers of fluid; said containers in said reservoir system are disposed in a predetermined configuration; and, (b) a fluid transfer system in fluid connection with said reservoir system, said fluid transfer system comprising: at least one fluid transfer head, adapted to transfer fluid from one of said plurality of reservoirs to an external tubing system; wherein each of said fluid transfer heads is characterized by a mechanism adapted to radially move each of said fluid transfer heads along said configuration of said containers.

According to one embodiment said predetermined configuration comprises a linear configuration, a radial configuration, an ellipsoidal configuration, a square configuration, a triangular configuration, a hexagonal configuration, a pentagonal configuration, any 2D or 3D shaped configuration and any combination thereof.

According to another embodiment, the fluid transfer system further comprising fluid regulating means, adapted to regulate at least one of the rate of transfer of fluid from said reservoir system to each of said fluid transfer heads or the pressure at which said fluid is transferred from said reservoir system to each of said fluid transfer heads.

According to another embodiment, the system further comprising a control system adapted to control at least one selected from a group consisting of (a) the rate of flow of fluid through said irrigation system according to a predetermined protocol; (b) the movement of said at least one fluid transfer head; (c) the activation of the same.

According to another embodiment, the system additionally comprising a pressure building system selected from pumping means adapted to withdraw said fluid from at least one of said containers; or pressure applying means adapted to apply pressure on at least one of said containers.

According to another embodiment, said system further comprising a pumping system in fluid connection with said fluid transfer system, adapted to withdraw said fluid from at least one of said containers of fluid in a predetermined rate of flow to an outer tubing system.

According to another embodiment, said system further comprising pressure applying means adapted to apply pressure on at least one of said containers of fluid so as to enable a predetermined rate of flow from at least one of said containers to an outer tubing system.

According to another embodiment, said pressure applying means is selected from a group consisting of a membrane encapsulating at least one of said containers of fluid, squeezing means adapted to apply squeezing pressure on at least one of said containers and any combination thereof and any combination thereof.

It is another object of the present invention the squeezing means are selected from pneumatic compression of at least one of the containers, hydrostatic compression of at least one of the containers, and any combination thereof.

According to one embodiment, the fluid is selected from a group consisting of gas, liquid and any combination thereof.

According to another embodiment, the fluid is selected from oxygen; anesthetic gas for use as local anesthesia, regional anesthesia and general anesthesia selected from ethers, halogenated ethers, desflurane (2,2,2-trifluoro-1-fluoroethyl-difluoromethyl ether, sevoflurane (2,2,2-trifluoro-1-[trifluoromethyl]ethyl fluoromethyl ether), and isoflurane (2-chloro-2-(difluoromethoxy)-1,1,1-trifluoro-ethane); blood; saline; glycine; water; plasma; medicament and any combination thereof.

According to another embodiment, several substantially different fluids are provided by the irrigation system of the present invention.

According to another embodiment, said substantially different fluids are provided to the patient in substantially the same amounts, different amounts, substantially the same rates, different rates, and any combination thereof.

The following description is provided while using a system with a pumping system, however, the same system can be provided with pressure applying means, adapted to apply pressure on at least one of said containers of fluid so as to enable a predetermined rate of flow from at least one of said containers to an outer tubing system.

Furthermore, the following description is provided to an irrigation system in which the containers are disposed in a linear configuration, however (as will be seen in FIGS. 13a-13c) a radial configuration can also be utilized.

Non-limiting examples of treatment protocols utilizing the system, according to at least some of the embodiments illustrated in the following description, are illustrated in examples 1-3.

According to the first protocol, at least two fluid transfer heads are provided, each of which is disposed in proximity to a container. The first is opened and fluid is extracted (either by pumping or by exerting force so as to extract fluid) until the fluid reaches a pre-determined level. Once said level is reached, the second container is pierced and fluid is extracted from the same. Once the level in the second container reaches a predetermined level, fluid is allowed to flow from the first container, while the second fluid transfer head moves to another container. Then said another container is spiked. Fluid flow from the first container is prevented and fluid flow from said second container is allowed.

In such a protocol, the second fluid transfer head moves from one container to the other while the first fluid transfer head (and the first container) is used as back up, ensuring continuous flow during the time the second fluid transfer head moves between one container and another.

In the second treatment protocol both the fluid transfer heads are moved. Thus, once the first container reaches a predetermined level, the fluid from the second container is allowed to flow and the fluid from the first is blocked. Then the first fluid transfer head is moved to another container.

In the third treatment protocol only one fluid transfer head is utilized and the same contains an internal reservoir to be used when the same moves from one container to the other.

Reference is now made to FIG. 1, which provides a schematic assembly diagram of an embodiment 1 of the apparatus disclosed herein. The apparatus comprises four subsystems, reservoir system 10, fluid transfer system 20, pumping system 30, and control system 40.

Reservoir system 10 comprises a plurality of supports 100 which are supported on at least two sides by support structure 110. In preferred embodiments of the invention, the supports are shelves, but any alternative means known in the art for supporting a plurality of containers may be used (e.g., drawer, receptacle, a sliding receptacle, chamber and any combination thereof). In the embodiment illustrated in FIG. 1, support structure 110 comprises three side walls along with a top and bottom. In other embodiments (not illustrated), the support structure also includes a fourth side wall, which can be opened (i.e. functions as a door) or removed in order to provide access to the supports in order to insert and remove containers, and then closed or replaced in order to prevent accidental disconnection or puncture while the apparatus is in use.

In preferred embodiments of the invention, supports 100 are placed at an angle other than horizontal in order to ease access. In more preferred embodiments, they are hingeably or pivotally attached to the walls so that the user may rotate at least partially each support about its long axis. Means for creating such rotatable supports (either rotatable individually or in tandem) are well-known in the art. The supports are of a sufficient area to support the containers used; as a non-limiting example, in typical embodiments, the containers will be standard prepackaged plastic bags of the fluid to be transferred. A slot 120 is located proximate to each support in at least one of the walls of the support structure. The slots extend to one edge of the wall, and are of a size appropriate at least to allow means for transferring fluid from the container to pass through. In preferred embodiments, the slots are adapted for use with containers that comprise a neck or cover or cap, and each slot is placed at a height relative to the nearest support such that, when the container lies on the support, the neck or cover or cap passes through the slot. In most preferred embodiments, the slots are of a size adapted for use with connectors that fix the position of the container, as described in detail below.

It should be emphasized that according to some embodiments, the system is provided with a dedicated connector to mate between the containers and the fluid transfer heads. According to another embodiment, the connector is reversibly coupled to the system and may be replaced from time to time.

The fluid transfer system 20 comprises a plurality of fluid transfer heads 200 and a support system 210 for the fluid transfer heads. As shown in FIG. 1, a typical support system comprises at least one vertical rod, the entire assembly being fixed to a base 220 (and in some embodiments cross pieces for additional support). In preferred embodiments, the base is fixed at a predetermined distance from the reservoir system, e.g. by fixing both systems to a common base.

Figure 2:
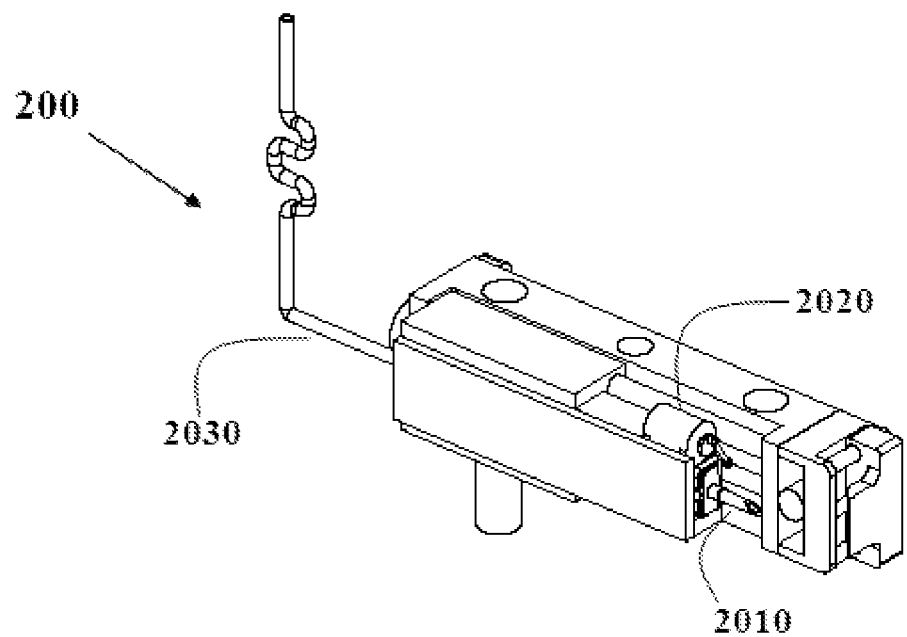
FIG. 2 illustrates a fluid transfer head according to one embodiment of the invention disclosed herein.

Reference is now made to FIG. 2, which presents a schematic illustration of a typical embodiment of a fluid transfer head. The fluid transfer head comprises a hollow needle 2010 (e.g., a spike) mounted therein and means 2020 for ejecting and retracting the needle (e.g., a spike). Such means are well-known in the art. The needle is in fluid connection (e.g. by a length of flexible tubing) with outlet 2030. In addition, the fluid transfer head contains means (not shown in FIG. 2) for adjusting and fixing the height of the fluid transfer head along support structure 210. In preferred embodiments, the means for adjusting and fixing the height comprises a stepper motor, but any other means for doing so known in the art may be used. The height adjusting and fixing means are used to bring the fluid transfer head (more particularly the needle contained within) to the height of one of the containers located within the reservoir system. In preferred embodiments, the height fixing means additionally comprises means for locking the fluid transfer head in place.

It should be emphasized that the spike is not an integral part of the system; but is a single use spike that is, prior to the use of the system, coupled to the same.

Furthermore, it should be emphasized that the piercing of the container might be achieved by either the movement of the spike on the fluid transfer heads to the container and/or the movement of the entire fluid transfer heads along with the spike.

Pumping system 30 includes any appropriate pumping means (including flow due to gravity) for pumping the fluid from the reservoir to its ultimate destination in the quantities and flow rates required for the specific use to which the apparatus is being put (e.g. irrigation during a particular medical procedure). In preferred embodiments, the pumping system comprises a peristaltic pump and flexible tube made of a material appropriate for use with a peristaltic pump and of a diameter appropriate for use with the peristaltic pump and for providing sufficient conductance to allow the fluid to flow at the desired rate. The tubing connections used in typical embodiments are described in detail below.

In further reference to FIG. 1, a managing and control system 40 includes means for directing the system in the tasks that it performs. In preferred embodiments of the invention, control system 40 comprises a computer preprogrammed to direct the system in these tasks. The computer communicates with the components of the system by any appropriate means known in the art (e.g. USB, parallel or serial connections, wireless connections, etc.). The control system is responsible for control of the vertical position of the fluid transfer heads, the status (retracted or ejected) of the needles, and the rate of flow of the fluid through the system. In preferred embodiments, it also monitors system parameters such as the amount of fluid within each container and whether the flow is at its programmed level. In the most preferred embodiments of the invention, the control system also includes means for notifying the operator of the current status of system parameters such as the beginning of pumping of fluid from the last of the containers; failure of one of the system components; a drop in the rate of flow of fluid below a predetermined threshold; a drop in the level of fluid in a predetermined container below a predetermined threshold; and so on. In the most preferred embodiments, the control system also includes a "panic button" that enables the operator to stop all flow of fluid through the system.

According to another embodiment, the system may communicate parameters associated with the system or the condition of the container (full, empty, etc.) to any wirelessly or wiredly connected system (remote computer, cellular system etc.) so as to inform/update/call for human backup (e.g., nurse) to replace/add/remove containers.

In some embodiments of the invention, it also includes a manual backup system comprising at least one container of fluid in fluid connection with the output of the system, and a manual valve for opening and closing the container. In embodiments that include the manual backup system, in case of a total system failure or if the reservoir system empties, fluid will continue to flow from the containers composing the manual backup system while the automatic system is being attended to.

According to another embodiment, the system will enable the hanging or suspension of the containers at a predetermined height such that the fluid will flow by means of gravity.

Figure 3:
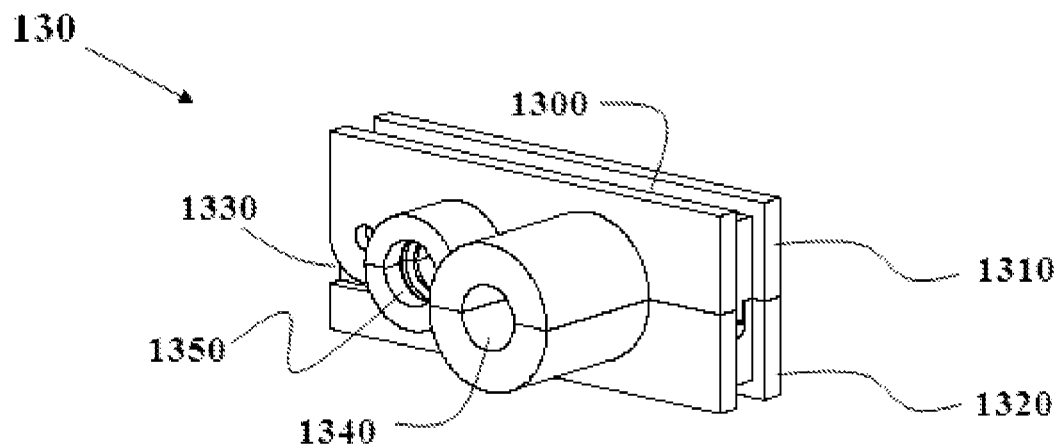
FIG. 3 presents a view of one embodiment of a connector for mating a fluid container's head to a fluid transfer head (namely, mating the neck and a nipple of the container's head to the neck and a nipple of the connector) and for fixing the position of the container according to one embodiment of the present invention.
Figure 3B:
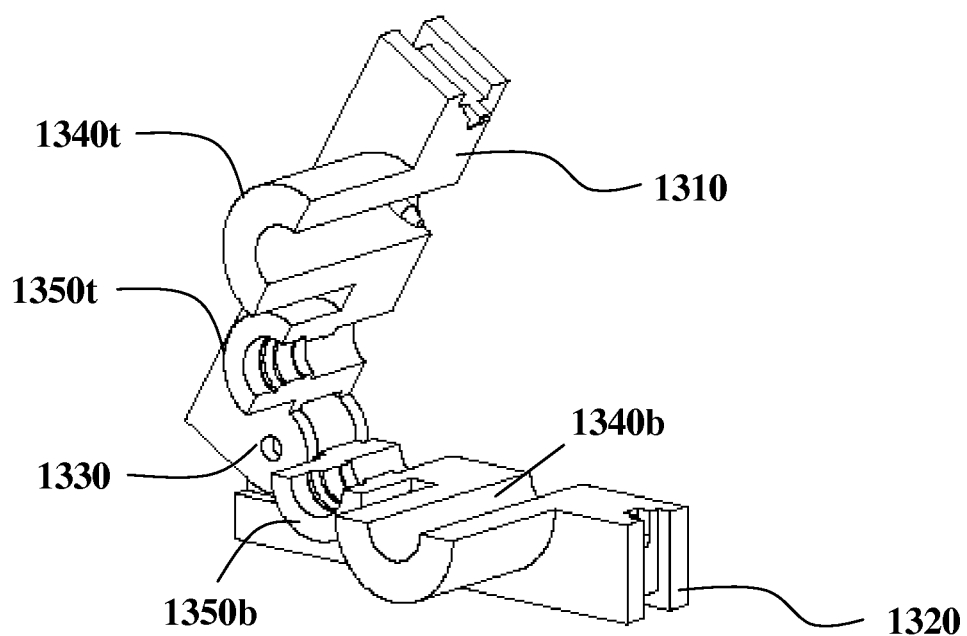

Reference is now made to FIG. 3, which illustrates one embodiment of connector 130. This connector fixes the position of the container within the reservoir system. The connector comprises an upper portion and a lower portion, and is of a size and shape (in preferred embodiments, rectangular) designed to be inserted into slot 120. As shown in FIG. 3, in preferred embodiments, the connector itself comprises a slot 1300 around its circumference of a depth appropriate for a slip fit into slot 120. Connector 130 comprises a lower section 1320 and an upper section 1310, connected by a hinge 1330 at the end first inserted into slot 120. In preferred embodiments, in its closed position, shown in FIG. 3A, the connector forms one or two hollow passageways 1340 and 1350. One (1340) is of a diameter sufficiently large that the neck of the container can fit through. Most commercially available containers comprise a nipple located near the neck. According to one embodiment, the second passageway (1350) in connector 130 accommodates this nipple, i.e. it has a diameter sufficiently large to allow the nipple to fit inside, and is separated from the first passageway by a distance substantially identical to that of the separation between the neck and the nipple of the container. Each of the two portions of the connector comprises two arcs such that when the connector is opened, as shown in FIG. 3B, the lower portion can support the neck (1340*b*) and nipple (1350*b*) of the container, while the upper portion comprises two matching arcs (1340*t* and 1350*t*, respectively). In preferred embodiments, each of the two portions of the connector comprises two semicircular arcs (i.e. the division between the two parts is along the diameters of the passageways).

It should be emphasized that the connector may be an integral part of the system, and may be a removable part enabled to couple to the system.

Figure 4A:
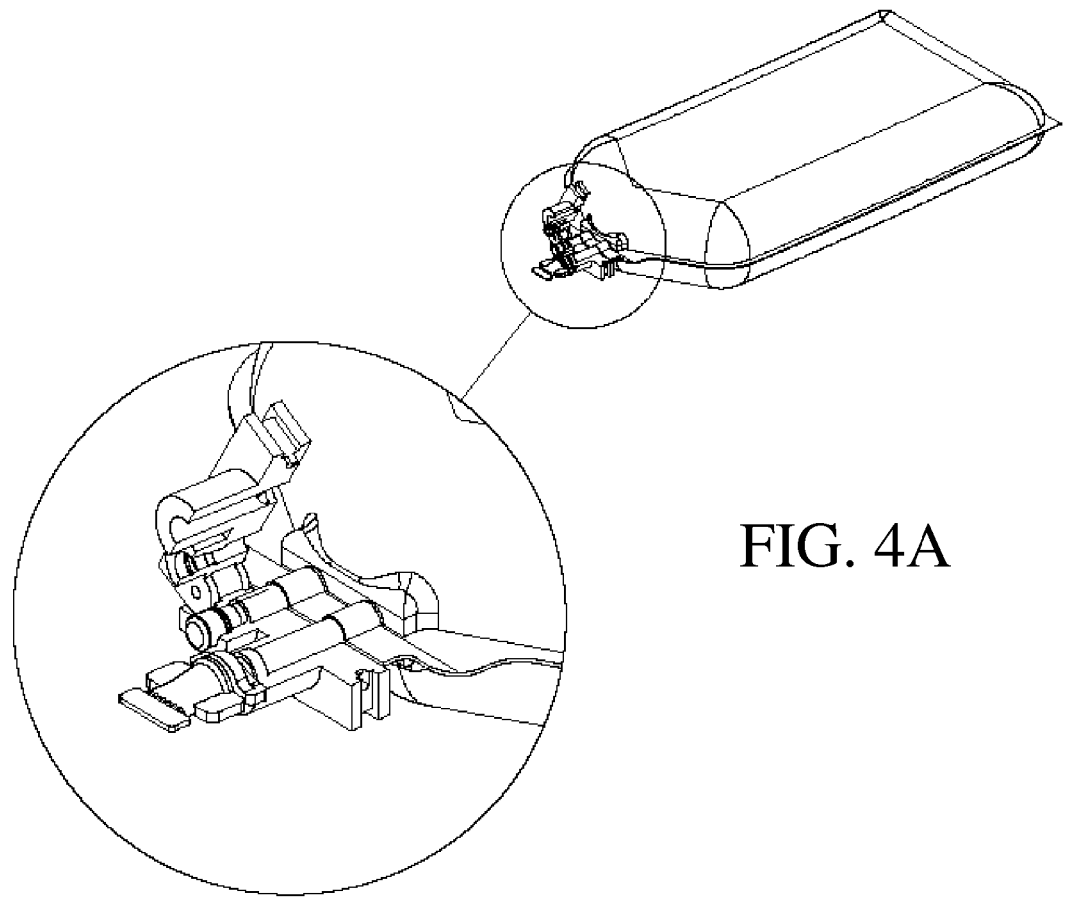
FIG. 4 illustrates the use of the component shown in FIG. 3.
Figure 4B:
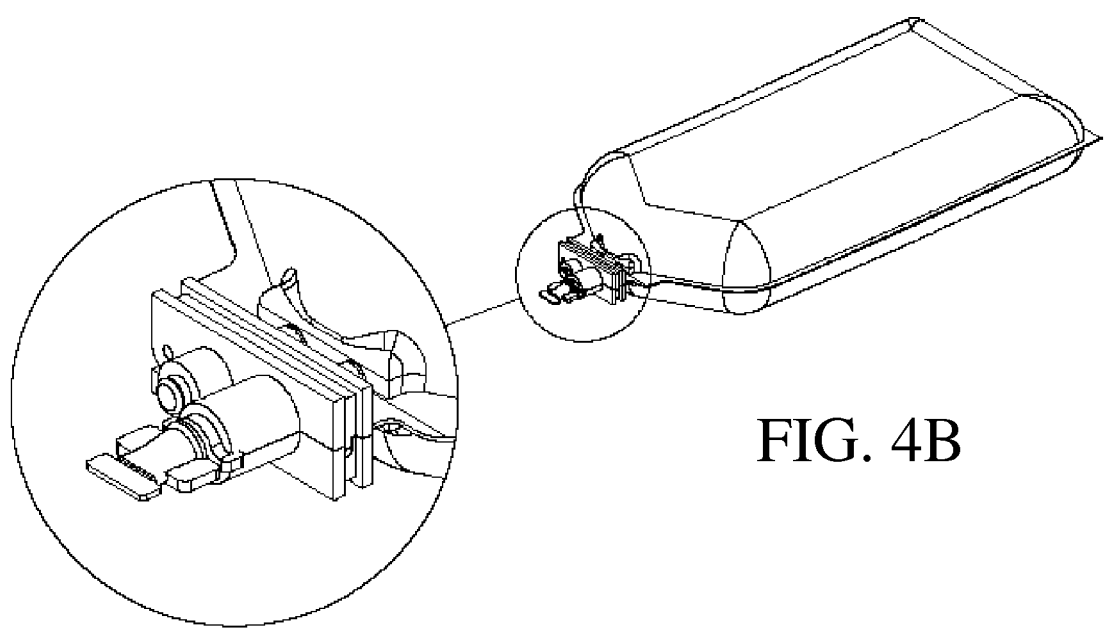

Reference is now made to FIG. 4, which illustrates the use of connector 130. The connector is opened and the container placed upon the lower portion such that the neck and nipple lie on and are supported by their respective arcs, as shown in FIG. 4A. The connector is then closed, forming the passageways and fixing the orientation of the container, as shown in FIG. 4B. The entire assembly is then slid into a slot 120, thus fixing both the location of the container and its rotational orientation.

Figure 5:
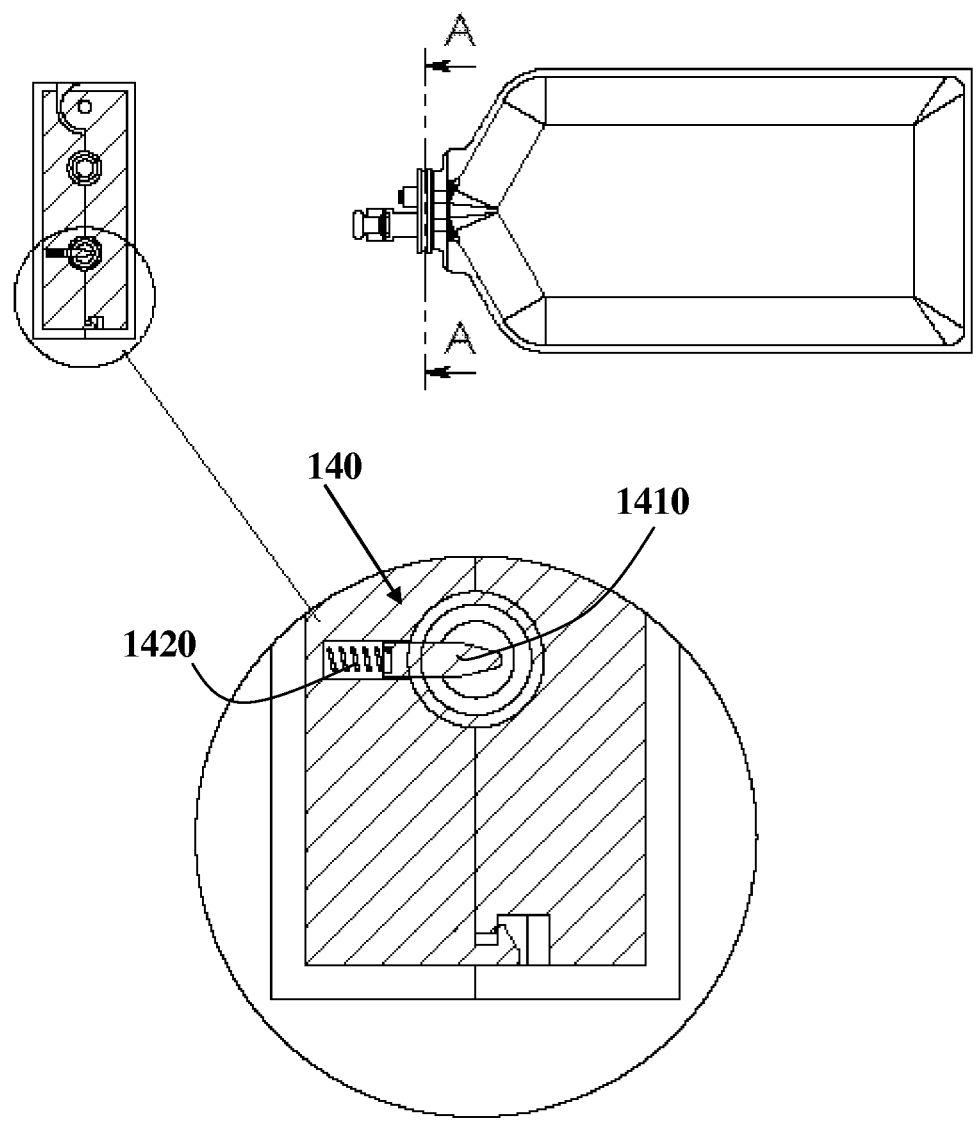
FIG. 5 illustrates a stopper mechanism for regulating the flow of fluid from a container according to one embodiment of the invention disclosed herein.

In preferred embodiments of the invention, the apparatus 130 also includes means for regulating the flow of the fluid, in particular, for preventing unwanted flow or leakage of fluid from a container when the spike is retracted. Reference is now made to FIG. 5, which illustrates a typical embodiment of these flow regulating means. In the embodiment illustrated in the figure, these means are located within connector 130. In this embodiment, the upper or lower portion of connector 130 comprises a passageway perpendicular to the passageway through which the neck of the container passes. Controller 140 passes through this passageway. The controller comprises member 1410 (e.g. a finger or pinch clamp) and actuating means (e.g. a retractable spring) 1420. When the actuating means are activated (e.g. the spring is extended), the member presses down on the neck of the container, thus closing it, while when the spring is retracted (the spike pushes the spring when ejected to the container), fluid flow from the container is possible.

Figure 6A:
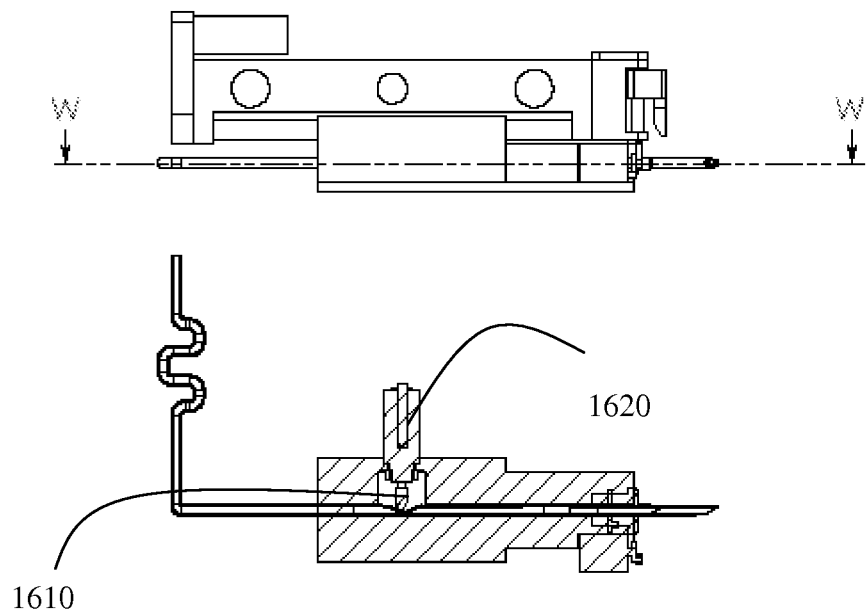
FIG. 6 illustrates a mechanism for regulating the flow of fluid from a container according to another embodiment of the invention disclosed herein.
Figure 6B:
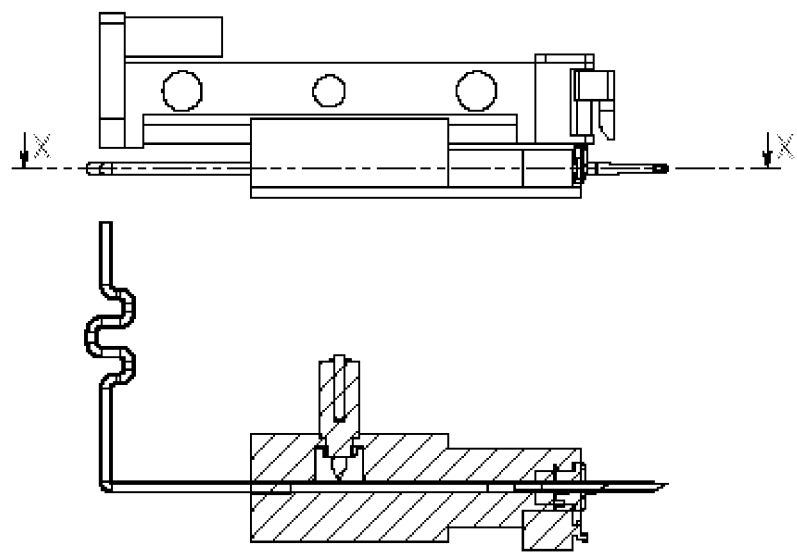

Reference is now made to FIG. 6, which shows a second embodiment of the flow regulating means. In this embodiment, the means are located within the fluid transfer head. A member 1610 and means for actuating it 1620 are located within the fluid transfer head. In this case, when the member is actuated (FIG. 6A), it closes off flow of fluid through the flexible tubing connecting needle 2010 to outlet 2030, while when it is open (FIG. 6B), flow of fluid through the fluid transfer head is unimpeded.

It should be emphasized that the member of FIG. 6 is adapted to apply pressure on the tubing so as to determine the rate of flow/pressure of the fluid.

Figure 7:
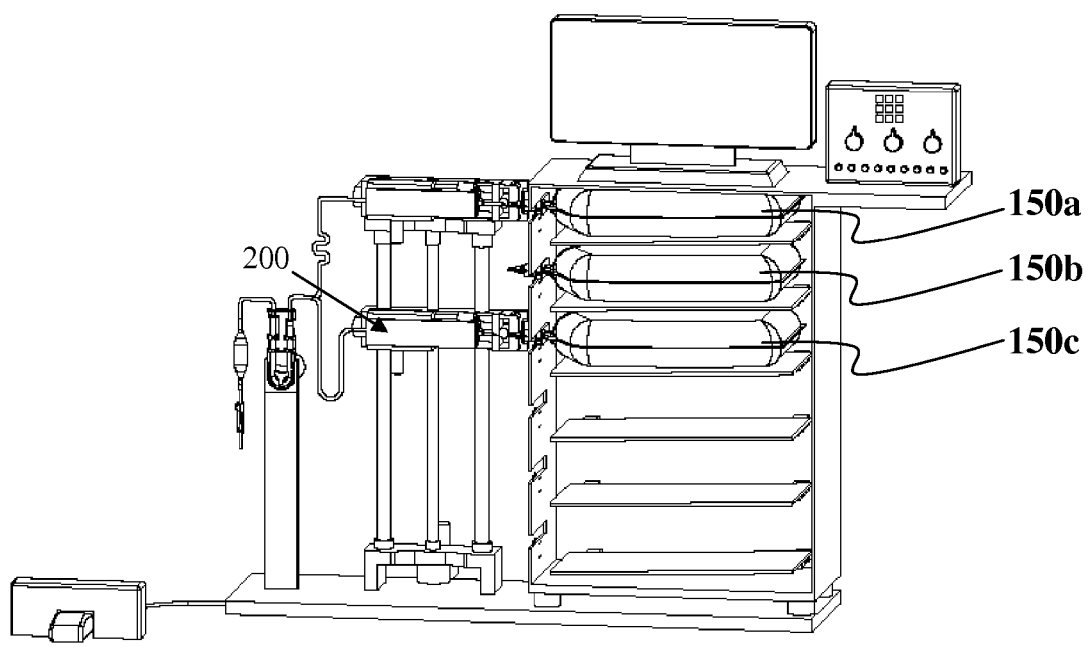
FIG. 7 presents a schematic assembly diagram of one embodiment of the apparatus disclosed herein, illustrating the placement of containers within the reservoir system.

Reference is now made to FIG. 7, which presents a schematic assembly diagram of apparatus 1 including a plurality of containers 150*a-c*. While this embodiment shows three containers inserted into a support system that can contain six, it will be clear to one skilled in the art that the size of the support system (and hence the maximum number of containers that can be contained within) is limited only by the space available to the support system. In the particular case of FIG. 7, the fluid transfer heads are withdrawing fluid from containers 150*a* and 150*c*; at another time during the particular operation, the second fluid transfer head 200 may have been moved to withdraw fluid from container 150*b*.

Figure 8:
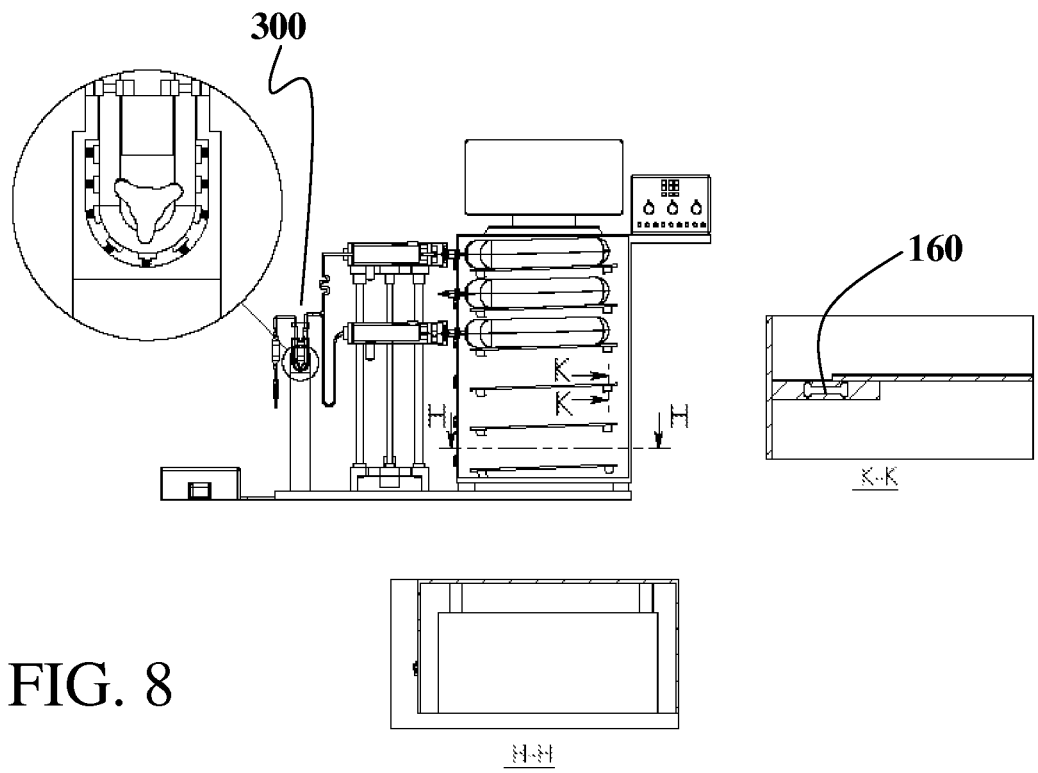
FIG. 8 presents a schematic assembly diagram of one embodiment of the apparatus disclosed herein that includes means for weighing the containers within the reservoir system.

In preferred embodiments of the invention, it includes means for determining the amount of fluid within each container. In most preferred embodiments, these means include means for measuring the weight of each container and determining the amount of fluid remaining from the current weight of the container relative to its weight when full. Reference is now made to FIG. 8, which illustrates one embodiment of such weight determining means. In this embodiment each support is in mechanical connection with actuator 160, which is located beneath support 100 (see FIG. 1). From the pressure upon the actuator, it is possible to calculate the weight according to procedures well known in the art, and, from the known density of the fluid, calculation of the volume of fluid remaining in the container is easily performed. Actuator 160 and its associated electronics are in communication with control system 40 (see FIG. 1), which calculates and records the weight of each container.

Figure 9:
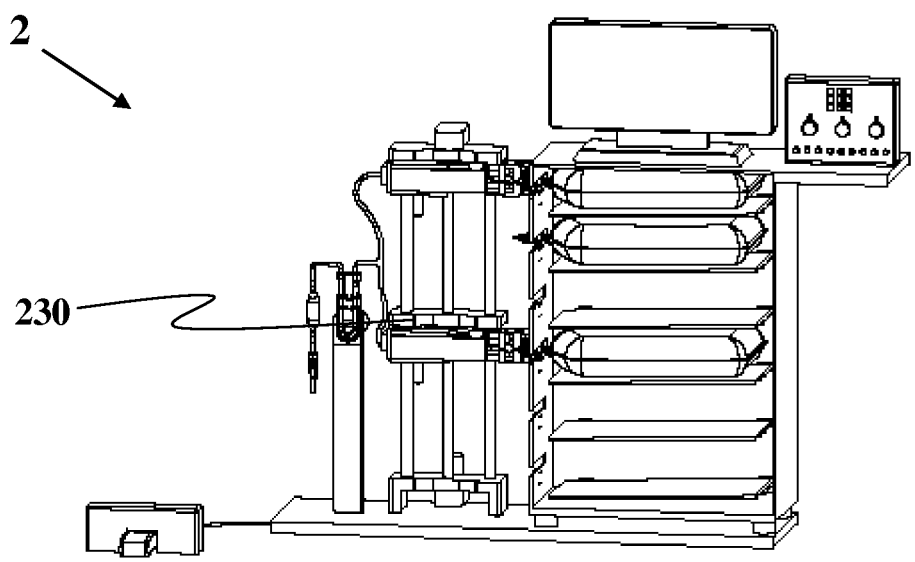
FIG. 9 presents a schematic assembly diagram of another embodiment of the apparatus disclosed herein.

Reference is now made to FIG. 9, which presents a schematic assembly diagram of a second embodiment 2 of the invention herein disclosed. In this embodiment, the fluid transfer system 20 (see FIG. 1) may further comprise horizontal stop 230. The horizontal stop acts to limit the motion of the fluid transfer heads. Thus, the upper of the at least two fluid transfer heads illustrated in FIG. 9 can only withdraw fluid from those containers located above the level of the horizontal stop, as the fluid transfer head cannot be lowered beyond the height of the stop. Similarly, the lower of the at least two fluid transfer heads can only withdraw fluid from the containers located below the level of the horizontal stop, as the fluid head cannot be raised beyond the height of the stop.

Figure 10A:
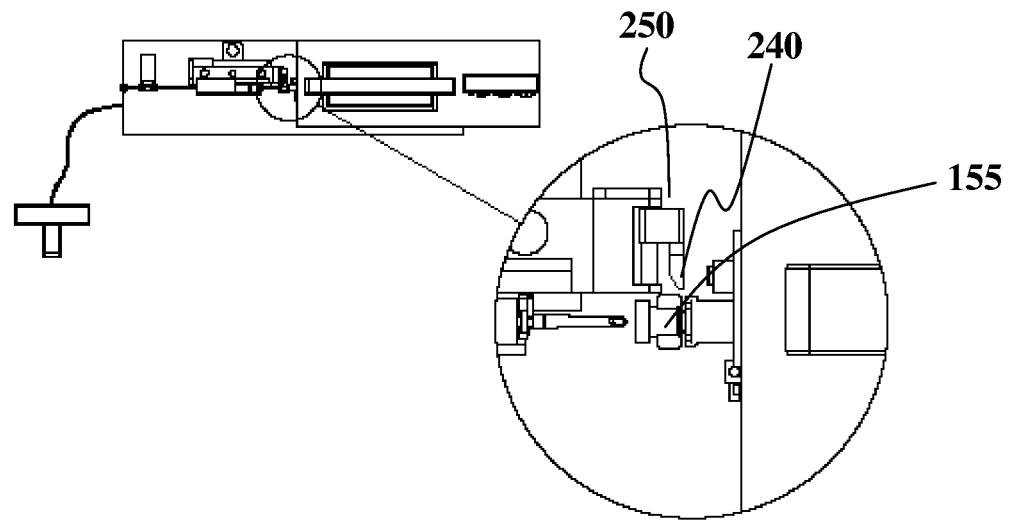
FIG. 10 illustrates means for removing a protective cover or cap from a container's head after the container is placed within the reservoir system; and, FIG. 11 illustrates the flexible tubing of fluid connections for the flow of the fluid from the containers to the exit from the apparatus according to one embodiment of the invention disclosed herein.
Figure 10B:
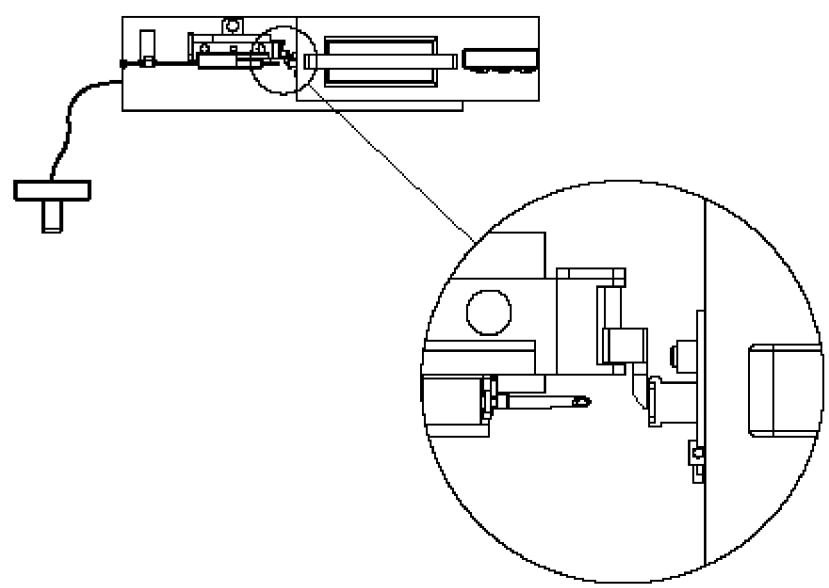
Figure 10C:
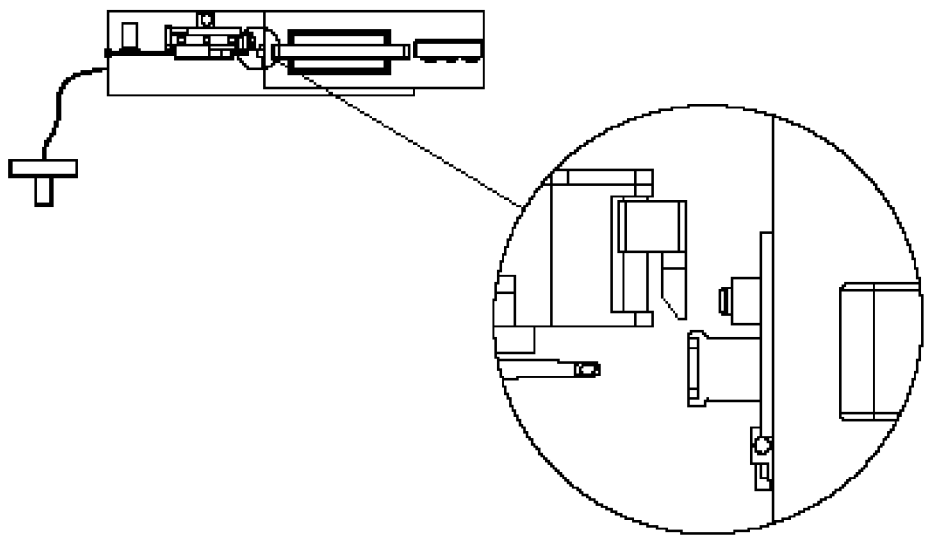
Figure 10D:
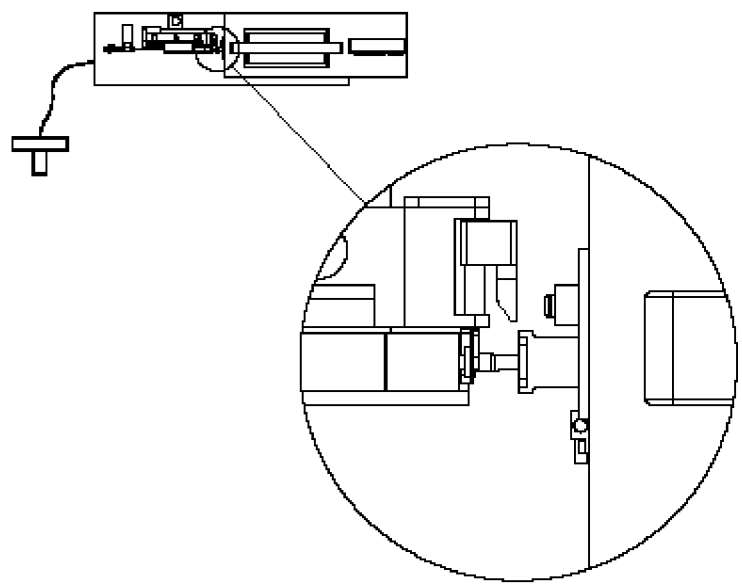

Most commercially available containers for fluids used in medical procedures, in particular plastic bags, comprise a protective plastic cover or cap that prevents accidental puncture of the neck. This protective plastic cover or cap must be removed before fluid can be withdrawn from the container. In preferred embodiments of the invention, it includes means for removing the protective plastic cover or cap after the container has been placed within the reservoir system. Reference is now made to FIG. 10, which illustrates one embodiment of such means. In the embodiment illustrated in the figure, the apparatus comprises cutting means 240 and an actuator 250 located between the fluid transfer head and the reservoir system. The actuator activates pushing means suitable for removing the plastic cap (155). FIG. 10A illustrates the system prior to removal of the protective plastic cap 155. As shown in FIG. 10B, upon actuation of the pushing means, it is lowered, thus removing the protective plastic cap. The actuator then retracts the cutting means, as shown in FIG. 10C. Once the cutting means have been retracted, needle 2010 can be ejected, piercing the container and permitting withdrawal of fluid, as shown in FIG. 10D.

Figure 10E:
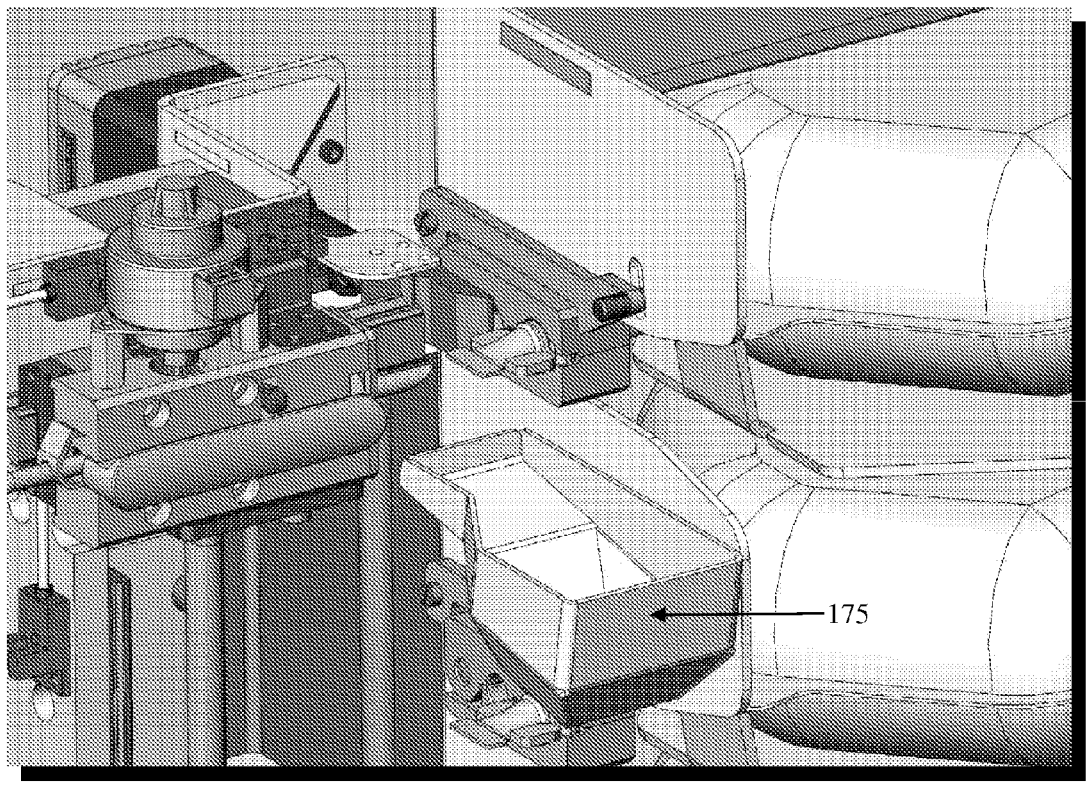

Reference is now made to FIG. 10E, which illustrates an embodiment of a holder (175) to hold the protective cap or cover after its removal from the fluid container, so that the cap or cover can neither litter the work area around the system nor interfere with the working of the system by falling into or jamming some part of the mechanism. The holder comprises a box or hopper with open top situated below the actuator and pushing means such that, after removal of the cap or cover from the container, said cap or cover falls, under the influence of gravity, into said holder. In preferred embodiments, the holder is situated a predetermined distance from said pushing means, preferably by being attached to said fluid transfer head. In some embodiments, the holder comprises a shallow inclined tray or other extension extending beneath the pushing means so that the cap or cover falls onto the tray and then slides from there into a deeper hopper, thereby ensuring that (a) the cap or cover is reliable captured, (b) there is sufficient storage space for all caps or covers removed from containers during even prolonged use of the system, and (c) the holder does not increase the amount of clearance needed between shelves in the system.

Figure 10F:
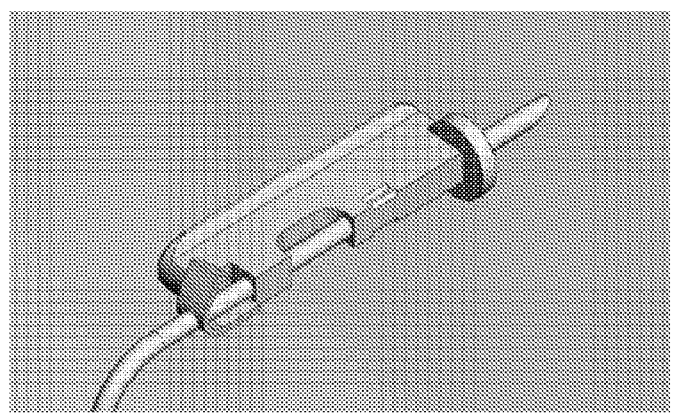
Figure 10G:
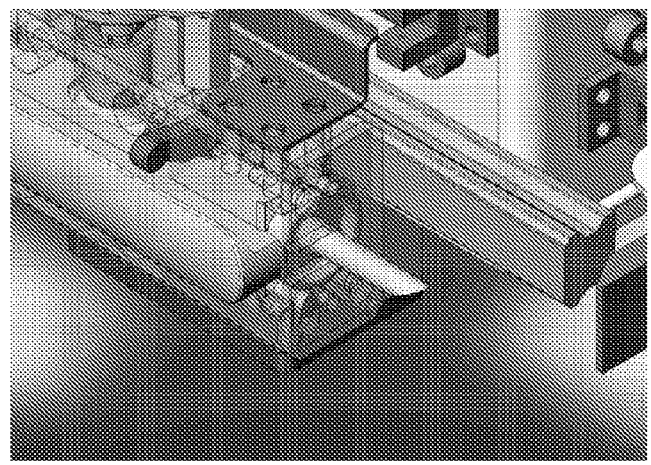

In general, the spike will be supplied with a protective cover to ensure both that the spike remains sterile and to prevent accidental needle sticks during transport, storage or mounting. It will be necessary to remove this protective cover before use of the spike and, in preferred embodiments, the cover will be removed before the spike is attached to the fluid transfer head and/or the tubing. Reference is now made to FIGS. 10E-10F which illustrate schematically embodiments of a connector in the fluid transfer head which couples the spike to the tubing. In the embodiment in FIG. 10E, the connector comprises a flange which prevents insertion of the spike into the spike-mounting mechanism if the protective cover has not been removed. FIG. 11F illustrates an embodiment wherein the spike must be inserted through an outer housing in the fluid transfer head, which is again not possible unless the protective cover has been removed. Said connector has the further advantage that it enables an operator to see that the spike is in the right position and is properly mounted.

In some embodiments, the system further comprises a mechanical stopper of any type known in the art, for non-limiting example, a pinch valve or wheel valve. This mechanical stopper enables the flow of fluid to be halted mechanically by an operator without altering any settings of the system. Such mechanical stoppage of the flow may be desirable, for example, to allow an operator to replace a spike that becomes blocked, to check the proper positioning of a spike, and to ensure that no leakage will occur during replacement of used containers. In preferred embodiments, said mechanical stopper is fluidly close to the spike. For non-limiting example, the fluid transfer head additionally comprises the mechanical stopper. In preferred embodiments, the connector additionally comprises a mechanical stopper.

Figure 11:
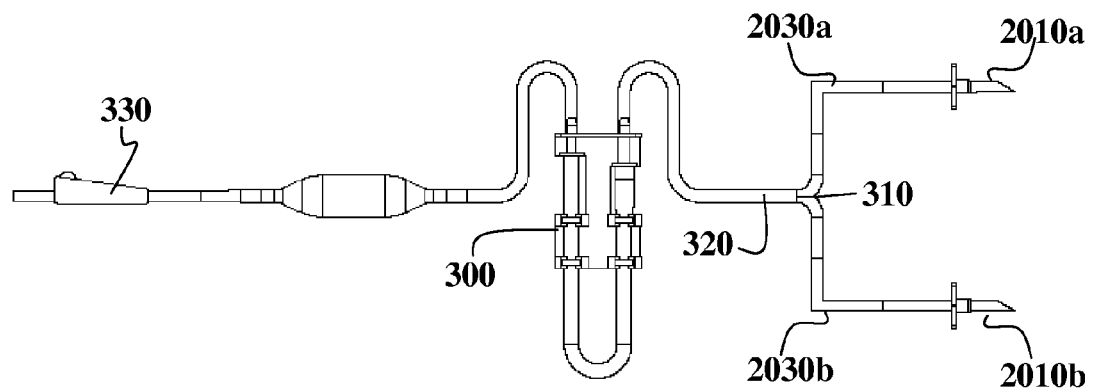

Reference is now made to FIG. 11, which illustrates schematically the fluid connections of a typical embodiment of the apparatus. Fluid connections are made through at least two fluid transfer heads from needles (e.g. spike) 2010*a* and 2010*b* to outlets 2030*a* and 2030*b*, respectively. The outlets are connected to flexible tubing, which is joined by a Y fitting 310 to form a single inlet 320 to a special tube and fittings that can connect to the pump 300. The fluid then passes through the pump to the final exit from the system (e.g. the site of the medical procedure) 330.

Figure 12A:
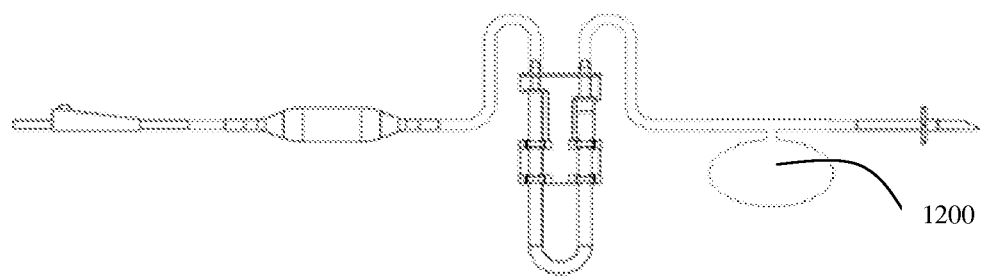
FIG. 12 illustrate another embodiment of the invention disclosed herein, in which an internal reservoir is utilized.
Figure 12B:
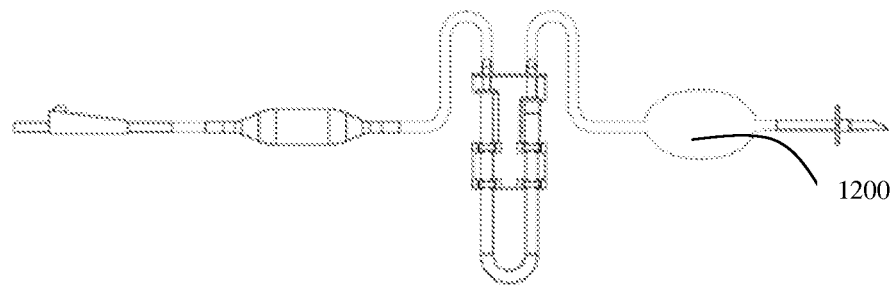
Figure 12C:
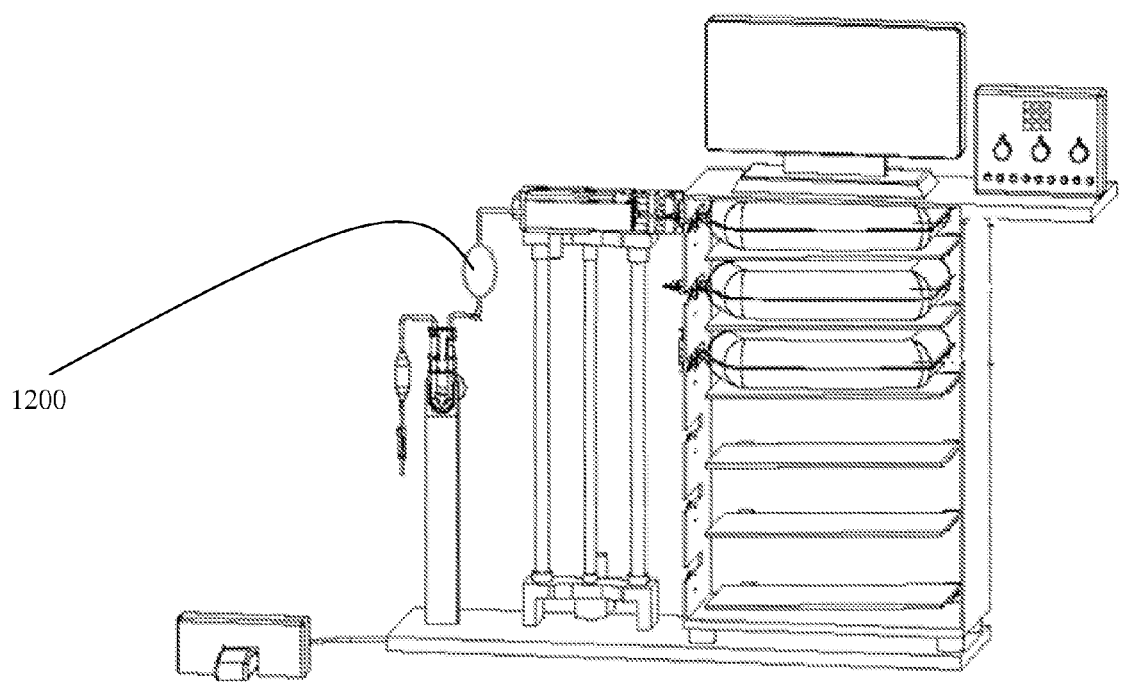

Reference is now made to FIGS. 12*a*-12*c* illustrating another embodiment of the present invention. FIGS. 12*a*-12*c* illustrate an embodiment in which at least one of the flexible tubing within at least one of the fluid transfer heads 200 comprises at least one internal reservoir 1200 for accommodating said fluid and for delivering said fluid while said fluid transfer head linearly moves along said main longitudinal axis of the Reservoir system 10 (i.e., from one container to another). Alternatively, as mentioned above, the fluid transfer head can radially move from one container to the other.

As mentioned above, each of said fluid transfer heads comprises:
a spike;
flexible tubing in fluid contact with said spike;
ejecting and retracting means for ejecting at least one of said spike and said fluid transfer head a predetermined minimum distance along the horizontal axis from a resting position to an ejected position and for retracting said at least one of said spike and said fluid transfer head from said ejected position to said resting position.
height fixing means adapted to fix the vertical position of said fluid transfer head.

According to this embodiment, said flexible tubing (of each of the fluid transfer heads) further comprises at least one internal reservoir for accommodating said fluid and for delivering said fluid while said fluid transfer head linearly moves along said main longitudinal axis.

Alternatively, according to this embodiment, said flexible tubing (of each of the fluid transfer heads) further comprises at least one internal reservoir for accommodating said fluid and for delivering said fluid while said fluid transfer head radially moves around said main longitudinal axis.

In another embodiment, the system is enabled to provide continuous irrigation to more than one patient simultaneously. In one embodiment of a system enabled to provide continuous irrigation to more than one patient simultaneously, each patient receives irrigation fluids from a separate container; the system comprises at least one fluid transfer head per patient to be provided with irrigation fluids. In another embodiment of a system enabled to provide continuous irrigation to more than one patient simultaneously, the tubing is divided so that one container will provide fluid to more than one patient, with valves on said tubing controlled by said computer program enabling control of flow of said irrigation fluids to said patients.

In another embodiment, the system is enabled to provide simultaneous continuous irrigation of more than one fluid to more than one patient.

Figure 14:
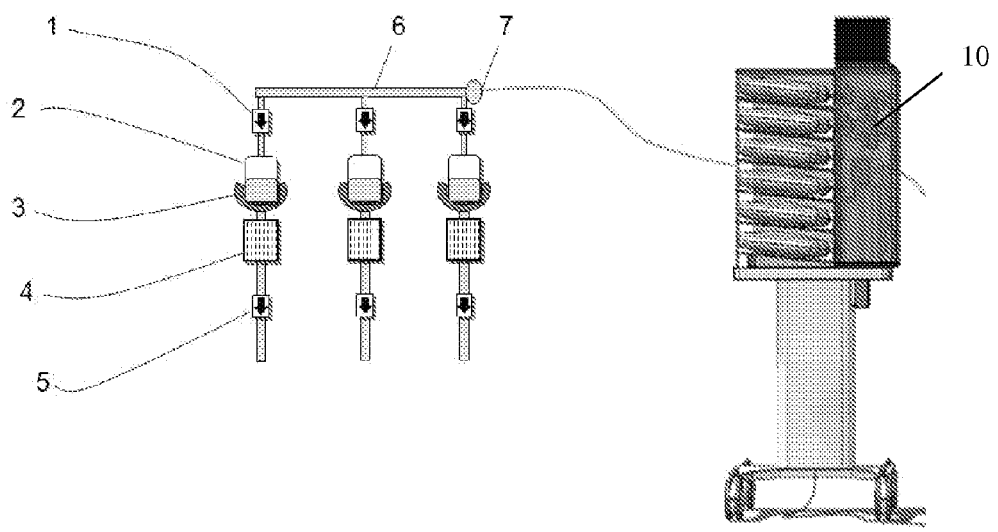
FIG. 14 illustrates another embodiment of the present invention.

In yet another embodiment, the system is enabled to provide continuous irrigation. Reference is now made to FIG. 14 illustrating said embodiment.

As illustrated in FIG. 14 the system as disclosed in any of the above, 10, may provide one or more fluids to one or more patients.

The system may e.g., comprise at least one tube 7 coupling the system 10 to the distribution manifold, 6.

At least one valve (e.g., a unidirectional valve) 1 is coupled to the distribution manifold, 6. Valve 1 is also coupled to at least one container 2, which is coupled to at least one sterilization mechanism 3 and/or at least one filter 4.

The sterilization mechanism 3 and the filter 4 may be coupled to a second valve (ensuring the right fluid is being delivered to the right patient).

According to such protocol the following steps are taken:
a. obtaining fluid extracting means;
b. obtaining one fluid transfer head, said fluid transfer head comprising:
 a spike;
 flexible tubing in fluid contact with said spike with internal reservoir;
 ejecting and retracting means for ejecting at least one of said spike and said fluid transfer head a predetermined minimum distance from a resting position to an ejected position and for retracting said at least one of said spike and said fluid transfer head from said ejected position to said resting position;
 a fluid exit in fluid contact with said flexible tubing; and,
 height fixing means adapted to fix the vertical position of said fluid transfer head; internal reservoir for accommodating said fluid and for delivering said fluid;
c. placing said fluid transfer head proximate to a first container from which pumping has not yet commenced;
d. connecting the fluid exits of said fluid transfer heads to said pumping means;
e. fixing the height of said fluid transfer head to the height of said first container, such that upon ejection of the spike, the wall of said first container will be pierced;
f. using said fluid regulating means to block flow of fluid from said fluid transfer head;
g. removing protective cover of said first container;
h. ejecting said spike into said fluid transfer head, thereby creating a fluid connection between the interior of said first container and said single outlet;
i. using said fluid regulating means to permit flow of fluid from said fluid transfer head;
j. actuating said pumping means;
k. filling said internal reservoir with said fluid;
l. extracting said fluid from said first container until the fluid level in said first container is reduced to a predetermined quantity;
m. using said fluid regulating means to block flow of fluid from said fluid transfer head;
n. extracting said fluid from the said internal reservoir;
o. retracting said spike into said fluid transfer head;
p. placing said fluid transfer head proximate to another available container;
q. fixing the height of said fluid transfer head to the height of said said another container, such that upon ejection of the spike, the wall of said another container will be pierced;
r. removing protective cover of said another container;
s. ejecting said spike of said fluid transfer head, thereby creating a fluid connection between the interior of said another container and said single outlet;
t. using said fluid regulating means to permit flow of fluid from said another fluid transfer head;
u. filling said internal reservoir with said fluid;
v. extracting said fluid from said container until the fluid level in said another container is reduced to a predetermined quantity;
repeating sequentially, for each of the remaining available containers, said steps of m-v.
Alternatively the following steps are taken:
a. obtaining fluid extracting means;
b. obtaining one fluid transfer head, said fluid transfer head comprising:
 a spike;
 flexible tubing in fluid contact with said spike with internal reservoir;
 ejecting and retracting means for ejecting at least one of said spike and said fluid transfer head a predetermined minimum distance from a resting position to an ejected position and for retracting said at least one of said spike and said fluid transfer head from said ejected position to said resting position;
 a fluid exit in fluid contact with said flexible tubing; and,
 height fixing means adapted to fix the vertical position of said fluid transfer head;
 internal reservoir for accommodating said fluid and for delivering said fluid;
c. placing said fluid transfer head proximate to a first container from which pumping has not yet commenced;

d. fixing the height of said fluid transfer head to the height of said first container, such that upon ejection of the spike, the wall of said first container will be pierced;
e. using said fluid regulating means to block flow of fluid from said fluid transfer head;
f. removing protective cover of said first container;
g. ejecting said spike of said fluid transfer head, thereby creating a fluid connection between the interior of said first container and said single outlet;
h. applying pressure on said first container so as to extract fluid from the same;
i. using said fluid regulating means to permit flow of fluid from said fluid transfer head;
j. filling said internal reservoir with said fluid;
k. extracting said fluid from said first container until the fluid level in said first container is reduced to a predetermined quantity;
l. using said fluid regulating means to block flow of fluid from said fluid transfer head;
m. discontinuing applying pressure on said first container from first fluid transfer head;
n. extracting said fluid from the said internal reservoir;
o. retracting said spike into said fluid transfer head;
p. placing said fluid transfer head proximate to another available container;
q. fixing the height of said fluid transfer head to the height of said said another container, such that upon ejection of the spike, the wall of said another container will be pierced;
r. removing protective cover of said another container;
s. ejecting said spike of said fluid transfer head, thereby creating a fluid connection between the interior of said another container and said single outlet;
t. applying pressure on said another container so as to extract fluid from the same;
u. using said fluid regulating means to permit flow of fluid from said another fluid transfer head;
v. filling said internal reservoir with said fluid;
w. extracting said fluid from said container until the fluid level in said another container is reduced to a predetermined quantity;
repeating sequentially, for each of the remaining available containers, said steps of l-w.

Figure 13A:
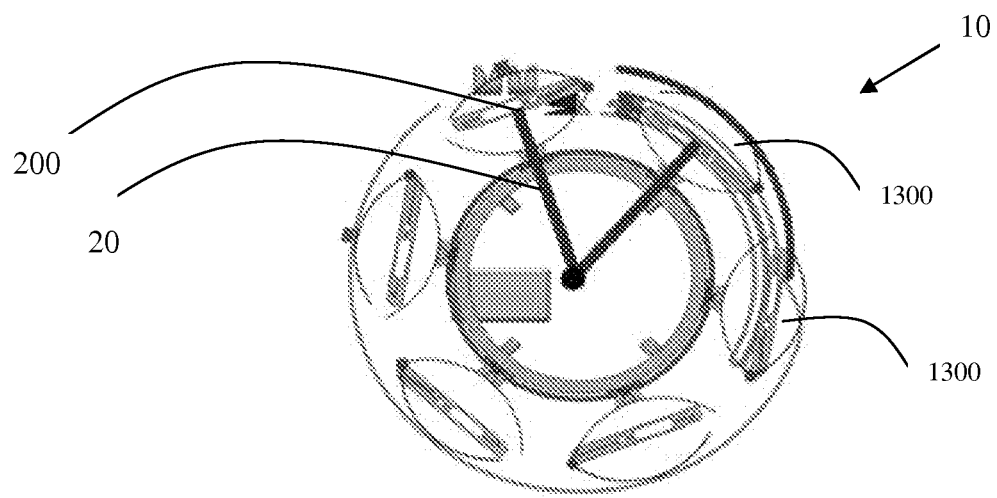
FIG. 13 illustrate another embodiment of the invention disclosed herein, in which a radial configuration of the container is utilized.
Figure 13B:
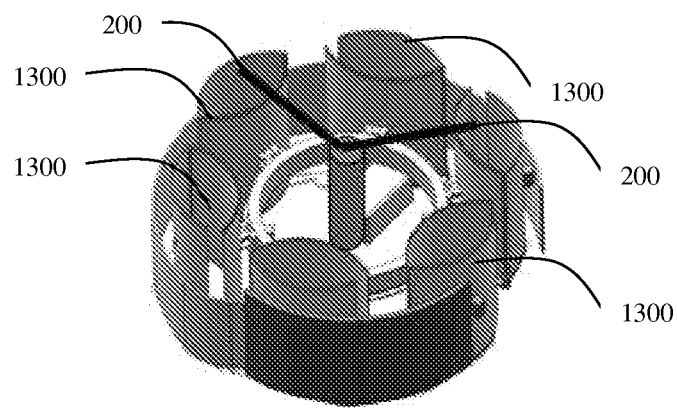
Figure 13C:
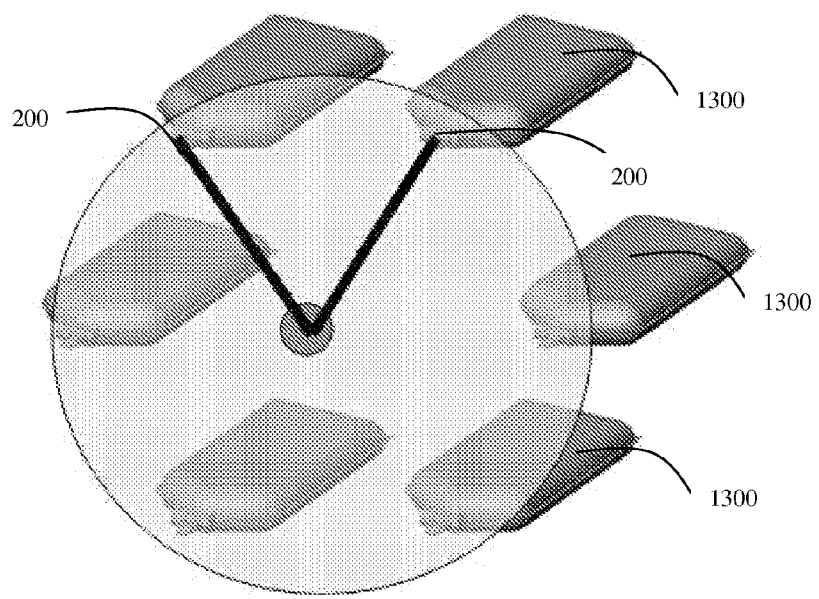

Reference is now made to FIG. 13 illustrating other embodiments of the present invention. FIG. 13 illustrates an embodiment in which the irrigation system for providing a continuous and controlled rate flow of a fluid, comprises (a) a reservoir system 10 comprising a plurality of containers 1300 of fluid reservoirs; said containers in said reservoir system 10 are disposed in a predetermined radial configuration; (b) a fluid transfer system 20 in fluid connection with said reservoir system, said fluid transfer system 20 comprising at least one fluid transfer head 200, adapted to transfer fluid from one of said plurality of reservoirs to an external tubing system; wherein each of said fluid transfer heads is characterized by a mechanism adapted to radially move each of said fluid transfer heads along said radial configuration of said containers. FIGS. 13a and 13b illustrate, in an out-of-scale manner, an embodiment wherein the main longitudinal axis is vertical, with FIG. 13a illustrating an embodiment of the system from above, while FIG. 13b illustrates a perspective view from above. FIG. 13c illustrates, in an out-of-scale manner, an embodiment wherein the main longitudinal axis is horizontal.

In the examples given below, for simplicity, the actions in each step are described as if they are happening continuously. It will be clear to one skilled in the art that there is no requirement for either continuousness or simultaneity and, indeed, in preferred embodiments of the invention, the actions will not in general be neither simultaneous nor continuous. For example, in a protocol that requires that a particular fluid transfer head be moved from one container to another, the movement can be (and in general will be) performed at any time that fluid is not actively flowing through that head.

Thus, it is one object of the present invention to provide an irrigation system for providing a continuous and controlled flow of a fluid, wherein said system comprises:
 a reservoir system comprising a plurality of containers of fluid; said reservoir system is characterized by a main longitudinal axis;
 a fluid transfer system in fluid connection with said reservoir system, said fluid transfer system comprising:
  at least one fluid transfer head, adapted to transfer fluid from one of said plurality of containers to an external tubing system; wherein each of said fluid transfer heads is characterized by a mechanism adapted to linearly move each of said fluid transfer heads along said main longitudinal axis.

It is another object of the present invention to provide an irrigation system for providing a continuous and controlled rate flow of a fluid, wherein said system comprises:
 a reservoir system comprising a plurality of containers of fluid; said containers in said reservoir system are disposed in a predetermined configuration;
 a fluid transfer system in fluid connection with said reservoir system, said fluid transfer system comprising:
  at least one fluid transfer head, adapted to transfer fluid from one of said plurality of containers to an external tubing system; wherein each of said fluid transfer heads is characterized by a mechanism adapted to radially move each of said fluid transfer heads.

It is another object of the present invention to provide the irrigation system as defined above, wherein said predetermined configuration is selected from a group consisting of a linear configuration, radial configuration, ellipsoidal, square, triangle, hexagonal, pentagonal, any 2D or 3D shape and any combination thereof.

It is another object of the present invention to provide the irrigation system as defined above, wherein said fluid transfer system further comprising fluid regulating means, adapted to regulate either the rate of transfer of fluid from said reservoir system to each of said fluid transfer heads or the pressure at which said fluid is transferred from said reservoir system to each of said fluid transfer heads.

It is another object of the present invention to provide the irrigation system as defined above, wherein said system further comprising a control system adapted to control at least one selected from a group consisting of (a) the rate of flow of fluid through said irrigation system according to a predetermined protocol; (b) the movement of said at least one fluid transfer head; (c) the activation of the same; and any combination thereof.

It is another object of the present invention to provide the irrigation system as defined above, wherein said system further comprising a pumping system in fluid connection with said fluid transfer system, adapted to withdraw said fluid from at least one of said containers of fluid in a predetermined rate of flow to an outer tubing system.

It is another object of the present invention to provide the irrigation system as defined above, wherein said system further comprising pressure applying means adapted to apply pressure on at least one of said containers of fluid so as to enable a predetermined rate of flow from at least one of said containers to an outer tubing system.

It is another object of the present invention to provide the irrigation system as defined above, wherein said pressure applying means is selected from a group consisting of a membrane encapsulating at least one of said containers of fluid, squeezing means adapted to apply squeezing pressure on at least one of said containers and any combination thereof and any combination thereof.

It is another object of the present invention to provide the irrigation system as defined above, wherein said squeezing means are selected from at least one of pneumatic, hydrostatic, and compression of at least one of the containers.

It is another object of the present invention to provide the irrigation system as defined above, wherein said fluid is selected from a group consisting of gas, liquid, and any combination thereof.

It is another object of the present invention to provide the irrigation system as defined above, wherein said fluid is selected from oxygen; anesthetic gas for use as local anesthesia, regional anesthesia and general anesthesia selected from ethers, halogenated ethers, desflurane (2,2,2-trifluoro-1-fluoroethyl-difluoromethyl ether, sevoflurane (2,2,2-trifluoro-1-[trifluoromethyl]ethyl fluoromethyl ether), and isoflurane (2-chloro-2-(difluoromethoxy)-1,1,1-trifluoro-ethane); blood; saline; glycine; water; plasma; medicament and any combination thereof.

It is another object of the present invention to provide the irrigation system as defined above, wherein said system is adapted to deliver several substantially different fluids.

It is another object of the present invention to provide the irrigation system as defined above, wherein said substantially different fluids are provided to said patient in substantially the same amounts, different amounts, substantially the same rates, different rates, and any combination thereof.

It is another object of the present invention to provide the irrigation system as defined above, wherein said fluid transfer system comprises at least at least two fluid transfer heads.

It is another object of the present invention to provide the irrigation system as defined above, wherein said at least one fluid transfer head comprises at least one internal reservoir for accommodating said fluid and for delivering said fluid while said fluid transfer head linearly moves along said main longitudinal axis.

It is another object of the present invention to provide the irrigation system as defined above, wherein said at least one fluid transfer head comprises at least one internal reservoir for accommodating said fluid and for delivering said fluid while said fluid transfer head radially moves around said main longitudinal axis.

It is another object of the present invention to provide the irrigation system as defined above, wherein said reservoir system comprises:
  a plurality of N support shelves adapted to support each of said containers of said fluid;
  support means adapted to support said shelves and to maintain a predetermined distance and orientation between each pair of shelves; and,
  a plurality of at least N slots in said shelf support means, said slots positioned such that at least one slot is located proximate to each of said N shelves.

It is another object of the present invention to provide the irrigation system as defined above, wherein said support is selected from a group consisting of shelf, drawer, receptacle, a sliding receptacle, chamber and any combination thereof.

It is another object of the present invention to provide the irrigation system as defined above, wherein said containers are bags made of a flexible material.

It is another object of the present invention to provide the irrigation system as defined above, wherein said containers are made of a rigid material.

It is another object of the present invention to provide the irrigation system as defined above, wherein said rigid material is glass, plastic, ceramic, metal, and any combination thereof.

It is another object of the present invention to provide the irrigation system as defined above, wherein said reservoir system further comprising monitoring means adapted to constantly monitor the amount of fluid extracted from said reservoir system and/or the amount of fluid remaining in said reservoir system and reporting means adapted to report the value of said determination.

It is another object of the present invention to provide the irrigation system as defined above, wherein said reservoir system further comprises weight measuring and reporting means adapted to determine the weight of each of said containers and to report the value of said determination.

It is another object of the present invention to provide the irrigation system as defined above, wherein said reservoir system further comprises volume measuring and reporting means adapted to determine the volume of each of said containers and to report the value of said determination.

It is another object of the present invention to provide the irrigation system as defined above, wherein said reservoir system further comprises at least one image sensor adapted to provide real time images of each of said containers.

It is another object of the present invention to provide the irrigation system as defined above, wherein said image sensor is selected from a group consisting of a camera, a video and any combination thereof.

It is another object of the present invention to provide the irrigation system as defined above, wherein said reservoir system further comprises at least one processing unit in communication with said at least one image sensor, adapted for real time image processing of said image such that either the volume or the weight of each of said containers is provided.

It is another object of the present invention to provide the irrigation system as defined above, wherein said reporting means is in communication with said control means.

It is another object of the present invention to provide the irrigation system as defined above, further comprising support rotation means adapted to allow rotation of each of said supports about an axis parallel to its longitudinal axis, said support rotation means further adapted to allow each of said supports to be fixed at an angle chosen by the operator of said irrigation system; said angle is adapted to be fixed prior to said irrigation, during said irrigation and any combination thereof.

It is another object of the present invention to provide the irrigation system as defined above, wherein said angle is in a range of about 0 degrees to about 90 degrees.

It is another object of the present invention to provide the irrigation system as defined above, wherein each of said containers comprises a neck and a nipple, and further wherein said irrigation system further comprises at least one connector between said container and said fluid transfer head, wherein said connector is reversibly coupled to said irrigation system and comprises:
a lower section comprising two arcs, the first of which is of a diameter and depth adapted to support said neck, and the second of which is of a diameter and depth adapted to support said nipple, the distance between the centers of said arcs substantially equal to the distance between the centers of said neck and said nipple; and, an upper section hingedly connected to said lower section, said upper section comprising two arcs of diameters substantially identical to those of the corresponding arcs of said lower section, said two arcs disposed such that closure of said hinged connection forms at least one circular hollow passageway passing through said connector.

It is another object of the present invention to provide the irrigation system as defined above, additionally comprising means adapted to fix said containers in place, to verify said containers are in place and any combination thereof.

It is another object of the present invention to provide the irrigation system as defined above, wherein said fluid transfer system further comprises fluid transfer head support means adapted to support said fluid transfer heads; said fluid transfer head support means adapted to allow vertical motion, radial motion and any combination thereof of at least one of said fluid transfer heads.

It is another object of the present invention to provide the irrigation system as defined above, wherein each of said fluid transfer heads comprises:

a spike;

flexible tubing in fluid contact with said spike;

ejecting and retracting means for ejecting at least one of said spike and said fluid transfer head a predetermined minimum distance along the horizontal axis from a resting position to an ejected position and for retracting said at least one of said spike and said fluid transfer head from said ejected position to said resting position.

height fixing means adapted to fix the vertical position of said fluid transfer head.

It is another object of the present invention to provide the irrigation system as defined above, wherein said flexible tubing further comprises at least one internal reservoir for accommodating said fluid and for delivering said fluid while said fluid transfer head linearly moves along said main longitudinal axis.

It is another object of the present invention to provide the irrigation system as defined above, wherein said flexible tubing further comprises at least one internal reservoir for accommodating said fluid and for delivering said fluid while said fluid transfer head radially moves around said main longitudinal axis.

It is another object of the present invention to provide the irrigation system as defined above, additionally comprising height fixing means adapted to fix the vertical position of said fluid transfer head or heads along said main longitudinal axis of said reservoir system.

It is another object of the present invention to provide the irrigation system as defined above, wherein at least one of said fluid transfer heads further comprises an actuator in mechanical contact with said fluid transfer head support means and in electronic connection with said control means, said actuator adapted to engage with said fluid transfer head support means, whereby actuation of said actuator by a command from said control means causes vertical motion of said fluid transfer head along the vertical axis of said fluid transfer support means through a distance determined by said control means.

It is another object of the present invention to provide the irrigation system as defined above, wherein said actuator comprises at least one selected from a group consisting of stepper motor, voice command actuator, motion detector and any combination thereof.

It is another object of the present invention to provide the irrigation system as defined above, wherein said fluid regulating means comprises:

pressure applying means mounted proximate to said flexible tubing in fluid contact with said spike; and, extending and retracting means in mechanical contact with said pressure applying means, said extending and retracting means adapted to reversibly extend said pressure applying means.

It is another object of the present invention to provide the irrigation system as defined above, wherein said fluid regulating means is adapted to activate or de-activate fluid flow in said irrigation system.

It is another object of the present invention to provide the irrigation system as defined above, wherein said extending and retracting means comprise a retractable spring.

It is another object of the present invention to provide the irrigation system as defined above, wherein said extending and retracting means are actuated by a means chosen from the group consisting of manual, mechanical, electrical, pneumatic, electromechanical, electropneumatic and any combination thereof.

It is another object of the present invention to provide the irrigation system as defined above, wherein said fluid regulating means comprises at least one selected from a group consisting of a pinch valve, a wheel-like shaped element adapted to apply pressure, and any combination thereof.

It is another object of the present invention to provide the irrigation system as defined above, wherein said pumping system comprises a peristaltic pump.

It is another object of the present invention to provide the irrigation system as defined above, wherein said pumping system comprises a single inlet, and further wherein at least two of said containers are in fluid connection with said single inlet.

It is another object of the present invention to provide the irrigation system as defined above, wherein two of said containers are in fluid connection with a "Y" joint located downstream of said fluid transfer heads.

It is another object of the present invention to provide the irrigation system as defined above, wherein said control system comprises a computer in communication with at least one of said reservoir system, said fluid transfer system, and said pumping system, and further wherein said control system is adapted to direct the flow of fluid through said system.

It is another object of the present invention to provide the irrigation system as defined above, further comprising:

at least one additional container in fluid connection with said pumping means; means for opening and closing said fluid connection; and, a rack adapted to hang said additional containers.

It is another object of the present invention to provide the irrigation system as defined above, further comprising an emergency shutoff switch adapted to halt flow of fluid through said irrigation system.

It is another object of the present invention to provide the irrigation system as defined above, wherein said control system is adapted to prevent over pressure of said fluid in said irrigation system.

It is another object of the present invention to provide the irrigation system as defined above, wherein said over pressure is prevented by means of at least one pressure sensor located in said pumping system.

It is another object of the present invention to provide the irrigation system as defined above, wherein said over pressure is prevented by means of at least one pressure sensor in communication with said outer tubing system.

It is another object of the present invention to provide the irrigation system as defined above, wherein said over pressure is prevented by means of at least one pressure sensor located within said outer tubing system.

It is another object of the present invention to provide the irrigation system as defined above, wherein said over pressure is prevented by means of at least one pressure sensor surrounding at least a portion of said outer tubing system.

It is another object of the present invention to provide the irrigation system as defined above, wherein said over pressure is prevented by means of limiting the pumping system to predetermined values.

It is another object of the present invention to provide the irrigation system as defined above, further including removing means for removing a protective cover or cap from said container.

It is another object of the present invention to provide the irrigation system as defined above, additionally comprising an automatic collecting means adapted to collect said cover or cap from said irrigation system.

It is another object of the present invention to provide the irrigation system as defined above, wherein said removing means comprise cutting means and actuating means adapted to actuate said cutting means.

It is another object of the present invention to provide the irrigation system as defined above, wherein said removing means comprise pressure applying means, adapted to apply pressure on said cover or cap by at least one of a group consisting of pulling, pushing and twisting said cover or cap.

It is another object of the present invention to provide a method for providing a substantially continuous and controlled flow of a fluid from a reservoir that comprises plurality of N containers, each of said N containers at a predetermined height and location, wherein said method comprises:
  a. obtaining fluid extracting means;
  b. obtaining at least two fluid transfer heads, each of said fluid transfer heads comprising:
    a spike;
    flexible tubing in fluid contact with said spike;
    ejecting and retracting means for ejecting at least one of said spike and said fluid transfer head a predetermined minimum distance from a resting position to an ejected position and for retracting said at least one of said spike and said fluid transfer head from said ejected position to said resting position;
    a fluid exit in fluid contact with said flexible tubing; and,
    height fixing means adapted to fix the vertical position of said fluid transfer head;
  c. placing a first fluid transfer head proximate to a first container;
  d. placing a second fluid transfer head proximate to a second container from which pumping has not yet commenced;
  e. connecting the fluid exits of said fluid transfer heads to a single outlet, and to said pumping means;
  f. fixing the height of said second fluid transfer head to the height of said second container, such that upon ejection of the spike, the wall of said second container will be pierced;
  g. using said fluid regulating means to block flow of fluid from said first fluid transfer head;
  h. using said fluid regulating means to block flow of fluid from said second fluid transfer head;
  i. removing protective cover of said first container;
  j. ejecting said spike of said first fluid transfer head, thereby creating a fluid connection between the interior of said first container and said single outlet;
  k. removing protective cover of the second container;
  l. ejecting said spike of said second fluid transfer head, thereby creating a fluid connection between the interior of said second container and said single outlet;
  m. using said fluid regulating means to permit flow of fluid from said first fluid transfer head;
  n. actuating said pumping means;
  o. extracting said fluid from said first container until the fluid level in said first container is reduced to a predetermined quantity;
  p. using said fluid regulating means to permit flow of fluid from said second fluid transfer head;
  q. using said fluid regulating means to block flow of fluid from said first fluid transfer head;
  r. extracting said fluid from said second container until the fluid level in said second container is reduced to a predetermined quantity;
  s. using said fluid regulating means to permit flow of fluid from said first fluid transfer head;
  t. using said fluid regulating means to block flow of fluid from said second fluid transfer head;
  u. retracting said spike into said second fluid transfer head;
  v. placing said second fluid transfer head proximate to another available container;
  w. fixing the height of said second fluid transfer head to the height of said said another container, such that upon ejection of the spike, the wall of said another container will be pierced;
  x. removing protective cover of said another container;
  y. ejecting said spike of said second fluid transfer head, thereby creating a fluid connection between the interior of said another container and said single outlet;
  z. using said fluid regulating means to permit flow of fluid from said second fluid transfer head;
  za. using said fluid regulating means to block flow of fluid from said first fluid transfer head;
  zb. extracting said fluid from said another container until the fluid level in said another container is reduced to a predetermined quantity;
  repeating sequentially, for each of the remaining containers, said steps of s-zb It is another object of the present invention to provide a method for providing a substantially continuous and controlled flow of a fluid from a reservoir that comprises plurality of N containers, each of said N containers at a predetermined height and location, wherein said method comprises:
  a. obtaining fluid extracting means;
  b. obtaining at least two fluid transfer heads, each of said fluid transfer heads comprising:
    a spike;
    flexible tubing in fluid contact with said spike;
    ejecting and retracting means for ejecting at least one of said spike and said fluid transfer head a predetermined minimum distance from a resting position to an ejected position and for retracting said at least one of said spike and said fluid transfer head from said ejected position to said resting position;
    a fluid exit in fluid contact with said flexible tubing; and,
    height fixing means adapted to fix the vertical position of said fluid transfer head;
  c. placing a first fluid transfer head proximate to a first container;
  d. placing a second fluid transfer head proximate to a second container from which pumping has not yet commenced;
  e. connecting the fluid exits of said fluid transfer heads to a single outlet;

f. fixing the height of said second fluid transfer head to the height of said second container, such that upon ejection of the spike, the wall of said second container will be pierced;
g. using said fluid regulating means to block flow of fluid from said first fluid transfer head;
h. using said fluid regulating means to block flow of fluid from said second fluid transfer head;
i. removing protective cover of said first container;
j. ejecting said spike of said first fluid transfer head, thereby creating a fluid connection between the interior of said first container and said single outlet;
k. removing protective cover of the second container;
l. ejecting said spike of said second fluid transfer head, thereby creating a fluid connection between the interior of said second container and said single outlet;
m. applying pressure on said first container so as to extract fluid from the same;
n. using said fluid regulating means to permit flow of fluid from said first fluid transfer head;
o. extracting said fluid from said first container until the fluid level in said first container is reduced to a predetermined quantity;
p. applying pressure on said second container so as to extract fluid from the same;
q. using said fluid regulating means to permit flow of fluid from said second fluid transfer head;
r. using said fluid regulating means to block flow of fluid from said first fluid transfer head;
s. discontinuing applying pressure on said first container
t. extracting said fluid from said second container until the fluid level in said second container is reduced to a predetermined quantity;
u. applying pressure on said first container so as to extract fluid from the same;
v. using said fluid regulating means to permit flow of fluid from said first fluid transfer head;
w. using said fluid regulating means to block flow of fluid from said second fluid transfer head;
x. discontinuing applying pressure on said second container
y. retracting said spike into said second fluid transfer head;
z. placing said second fluid transfer head proximate to another available container;
za. fixing the height of said second fluid transfer head to the height of said said another container, such that upon ejection of the spike, the wall of said another container will be pierced;
zb. removing protective cover of said another container;
zc. ejecting said spike of said second fluid transfer head, thereby creating a fluid connection between the interior of said another container and said single outlet;
zd. applying pressure on said another container so as to extract fluid from the same;
ze. using said fluid regulating means to permit flow of fluid from said second fluid transfer head;
zf. using said fluid regulating means to block flow of fluid from said first fluid transfer head;
zg. discontinuing applying pressure on said first container
zh. extracting said fluid from said another container until the fluid level in said another container is reduced to a predetermined quantity;
repeating sequentially, for each of the remaining containers, said steps of u-zh It is another object of the present invention to provide a method for providing a substantially continuous and controlled flow of a fluid from a reservoir that comprises plurality of N containers, each of said N containers at a predetermined height and location, wherein said method comprises:
a. obtaining fluid extracting means;
b. obtaining at least two fluid transfer heads, each of said fluid transfer heads comprising:
a spike;
flexible tubing in fluid contact with said spike;
ejecting and retracting means for ejecting at least one of said spike and said fluid transfer head a predetermined minimum distance from a resting position to an ejected position and for retracting said at least one of said spike and said fluid transfer head from said ejected position to said resting position;
a fluid exit in fluid contact with said flexible tubing; and,
height fixing means adapted to fix the vertical position of said fluid transfer head;
c. placing a first fluid transfer head proximate to a first container from which pumping has not yet commenced;
d. placing a second fluid transfer head proximate to a second container from which pumping has not yet commenced;
e. connecting the fluid exits of said fluid transfer heads to a single outlet, and to said pumping means;
f. fixing the height of said first fluid transfer head to the height of said first container, such that upon ejection of the spike, the wall of said first container will be pierced;
g. fixing the height of said second fluid transfer head to the height of said second container, such that upon ejection of the spike, the wall of said second container will be pierced;
h. using said fluid regulating means to block flow of fluid from said first fluid transfer head;
i. using said fluid regulating means to block flow of fluid from said second fluid transfer head;
j. removing protective cover of said first container;
k. ejecting said spike of said first fluid transfer head, thereby creating a fluid connection between the interior of said first container and said single outlet;
l. removing protective cover of the second container;
m. ejecting said spike of said second fluid transfer head, thereby creating a fluid connection between the interior of said second container and said single outlet;
n. using said fluid regulating means to permit flow of fluid from said first fluid transfer head;
o. actuating said pumping means;
p. extracting said fluid from said first container until the fluid level in said first container is reduced to a predetermined quantity;
q. using said fluid regulating means to permit flow of fluid from said second fluid transfer head;
r. using said fluid regulating means to block flow of fluid from said first fluid transfer head;
s. extracting said fluid from said second container until the fluid level in said second container is reduced to a predetermined quantity;
t. retracting said spike into said first fluid transfer head;
u. placing said first fluid transfer head proximate to another available container;
v. fixing the height of said first fluid transfer head to the height of said said another container, such that upon ejection of the spike, the wall of said another container will be pierced;
w. removing protective cover of said another container;
x. ejecting said spike of said first fluid transfer head, thereby creating a fluid connection between the interior of said another container and said single outlet;

y. using said fluid regulating means to permit flow of fluid from said first fluid transfer head;
z. using said fluid regulating means to block flow of fluid from said second fluid transfer head;
za. extracting said fluid from said another container until the fluid level in said another container is reduced to a predetermined quantity
zb. retracting said spike into said second fluid transfer head;
zc. placing said second fluid transfer head proximate to another available container;
zd. fixing the height of said second fluid transfer head to the height of said said another container, such that upon ejection of the spike, the wall of said another container will be pierced;
ze. removing protective cover of said another container;
zf. ejecting said spike of said second fluid transfer head, thereby creating a fluid connection between the interior of said another container and said single outlet;
zg. using said fluid regulating means to permit flow of fluid from said second fluid transfer head;
zh. using said fluid regulating means to block flow of fluid from said first fluid transfer head;
zi. extracting said fluid from said another container until the fluid level in said another container is reduced to a predetermined quantity
repeating sequentially, for each of the remaining available containers and respective fluid transfer head, said steps of t-zi.

It is another object of the present invention to a method for providing a substantially continuous and controlled flow of a fluid from a reservoir that comprises plurality of N containers, each of said N containers at a predetermined height and location, wherein said method comprises:
a. obtaining fluid extracting means;
b. obtaining at least two fluid transfer heads, each of said fluid transfer heads comprising:
    a spike;
    flexible tubing in fluid contact with said spike;
    ejecting and retracting means for ejecting at least one of said spike and said fluid transfer head a predetermined minimum distance from a resting position to an ejected position and for retracting said at least one of said spike and said fluid transfer head from said ejected position to said resting position;
    a fluid exit in fluid contact with said flexible tubing; and,
    height fixing means adapted to fix the vertical position of said fluid transfer head;
c. placing a first fluid transfer head proximate to a first container from which pumping has not yet commenced;
d. placing a second fluid transfer head proximate to a second container from which pumping has not yet commenced;
e. connecting the fluid exits of said fluid transfer heads to a single outlet;
f. fixing the height of said first fluid transfer head to the height of said first container, such that upon ejection of the spike, the wall of said first container will be pierced;
g. fixing the height of said second fluid transfer head to the height of said second container, such that upon ejection of the spike, the wall of said second container will be pierced;
h. using said fluid regulating means to block flow of fluid from said first fluid transfer head;
i. using said fluid regulating means to block flow of fluid from said second fluid transfer head;
j. removing protective cover of said first container;
k. ejecting said spike of said first fluid transfer head, thereby creating a fluid connection between the interior of said first container and said single outlet;
l. removing protective cover of the second container;
m. ejecting said spike of said second fluid transfer head, thereby creating a fluid connection between the interior of said second container and said single outlet;
n. applying pressure on said first container so as to extract fluid from the same;
o. using said fluid regulating means to permit flow of fluid from said first fluid transfer head;
p. extracting said fluid from said first container until the fluid level in said first container is reduced to a predetermined quantity;
q. applying pressure on said second container so as to extract fluid from the same;
r. using said fluid regulating means to permit flow of fluid from said second fluid transfer head;
s. using said fluid regulating means to block flow of fluid from said first fluid transfer head;
t. discontinuing applying pressure on said first container
u. extracting said fluid from said second container until the fluid level in said second container is reduced to a predetermined quantity;
v. retracting said spike into said first fluid transfer head;
w. placing said first fluid transfer head proximate to another available container;
x. fixing the height of said first fluid transfer head to the height of said said another container, such that upon ejection of the spike, the wall of said another container will be pierced;
y. removing protective cover of said another container;
z. ejecting said spike of said first fluid transfer head, thereby creating a fluid connection between the interior of said another container and said single outlet;
za. applying pressure on said another container so as to extract fluid from the same;
zb. using said fluid regulating means to permit flow of fluid from said first fluid transfer head;
zc. using said fluid regulating means to block flow of fluid from said second fluid transfer head;
zd. discontinuing applying pressure on said second container
ze. extracting said fluid from said another container until the fluid level in said another container is reduced to a predetermined quantity;
zf. retracting said spike into said second fluid transfer head;
zg. placing said second fluid transfer head proximate to another available container;
zh. fixing the height of said second fluid transfer head to the height of said said another container, such that upon ejection of the spike, the wall of said another container will be pierced;
zi. removing protective cover of said another container;
zg. ejecting said spike of said second fluid transfer head, thereby creating a fluid connection between the interior of said another container and said single outlet;
zk. applying pressure on said another container so as to extract fluid from the same;
zl. using said fluid regulating means to permit flow of fluid from said second fluid transfer head;
zm. using said fluid regulating means to block flow of fluid from said first fluid transfer head;
zn. discontinuing applying pressure on said another container from first fluid transfer head;

zo. extracting said fluid from said another container until the fluid level in said another container is reduced to a predetermined quantity repeating sequentially, for each of the remaining available containers and respective fluid transfer head, said steps of t-zo.

It is another object of the present invention to provide a method for providing a substantially continuous and controlled flow of a fluid from a reservoir that comprises plurality of N containers, each of said N containers at a predetermined height and location, wherein said method comprises:

a. obtaining fluid extracting means;
b. obtaining one fluid transfer head, said fluid transfer head comprising:
   a spike;
   flexible tubing in fluid contact with said spike with internal reservoir;
   ejecting and retracting means for ejecting at least one of said spike and said fluid transfer head a predetermined minimum distance from a resting position to an ejected position and for retracting said at least one of said spike and said fluid transfer head from said ejected position to said resting position;
   a fluid exit in fluid contact with said flexible tubing; and,
   height fixing means adapted to fix the vertical position of said fluid transfer head;
   internal reservoir for accommodating said fluid and for delivering said fluid;
c. placing said fluid transfer head proximate to a first container from which pumping has not yet commenced;
d. connecting the fluid exits of said fluid transfer heads to said pumping means;
e. fixing the height of said fluid transfer head to the height of said first container, such that upon ejection of the spike, the wall of said first container will be pierced;
f. using said fluid regulating means to block flow of fluid from said fluid transfer head;
g. removing protective cover of said first container;
h. ejecting said spike of said fluid transfer head, thereby creating a fluid connection between the interior of said first container and said single outlet;
i. using said fluid regulating means to permit flow of fluid from said fluid transfer head;
j. actuating said pumping means;
k. filling said internal reservoir with said fluid;
l. extracting said fluid from said first container until the fluid level in said first container is reduced to a predetermined quantity;
m. using said fluid regulating means to block flow of fluid from said fluid transfer head;
n. extracting said fluid from the said internal reservoir;
o. retracting said spike into said fluid transfer head;
p. placing said fluid transfer head proximate to another available container;
q. fixing the height of said fluid transfer head to the height of said said another container, such that upon ejection of the spike, the wall of said another container will be pierced;
r. removing protective cover of said another container;
s. ejecting said spike of said fluid transfer head, thereby creating a fluid connection between the interior of said another container and said single outlet;
t. using said fluid regulating means to permit flow of fluid from said another fluid transfer head;
u. filling said internal reservoir with said fluid;
v. extracting said fluid from said container until the fluid level in said another container is reduced to a predetermined quantity;

repeating sequentially, for each of the remaining available containers, said steps of m-v.

It is another object of the present invention to provide a method for providing a substantially continuous and controlled flow of a fluid from a reservoir that comprises plurality of N containers, each of said N containers at a predetermined height and location, wherein said method comprises:

a. obtaining fluid extracting means;
b. obtaining one fluid transfer head, said fluid transfer head comprising:
   a spike;
   flexible tubing in fluid contact with said spike with internal reservoir;
   ejecting and retracting means for ejecting at least one of said spike and said fluid transfer head a predetermined minimum distance from a resting position to an ejected position and for retracting said at least one of said spike and said fluid transfer head from said ejected position to said resting position;
   a fluid exit in fluid contact with said flexible tubing; and,
   height fixing means adapted to fix the vertical position of said fluid transfer head;
   internal reservoir for accommodating said fluid and for delivering said fluid;
c. placing said fluid transfer head proximate to a first container from which pumping has not yet commenced;
d. fixing the height of said fluid transfer head to the height of said first container, such that upon ejection of the spike, the wall of said first container will be pierced;
e. using said fluid regulating means to block flow of fluid from said fluid transfer head;
f. removing protective cover of said first container;
g. ejecting said spike of said fluid transfer head, thereby creating a fluid connection between the interior of said first container and said single outlet;
h. applying pressure on said first container so as to extract fluid from the same;
i. using said fluid regulating means to permit flow of fluid from said fluid transfer head;
j. filling said internal reservoir with said fluid;
k. extracting said fluid from said first container until the fluid level in said first container is reduced to a predetermined quantity;
l. using said fluid regulating means to block flow of fluid from said fluid transfer head;
m. discontinuing applying pressure on said first container from first fluid transfer head;
n. extracting said fluid from the said internal reservoir;
o. retracting said spike into said fluid transfer head;
p. placing said fluid transfer head proximate to another available container;
q. fixing the height of said fluid transfer head to the height of said said another container, such that upon ejection of the spike, the wall of said another container will be pierced;
r. removing protective cover of said another container;
s. ejecting said spike of said fluid transfer head, thereby creating a fluid connection between the interior of said another container and said single outlet;
t. applying pressure on said another container so as to extract fluid from the same;
u. using said fluid regulating means to permit flow of fluid from said another fluid transfer head;
v. filling said internal reservoir with said fluid;

w. extracting said fluid from said container until the fluid level in said another container is reduced to a predetermined quantity;

repeating sequentially, for each of the remaining available containers, said steps of l-w.

It is another object of the present invention to provide the method as defined above, additionally comprising step of removing at least one of the container's caps. (As written, it implies that each container has at least one cap, and may have more. If "containers' cap" it means one cap on each of several containers. If "containers' caps", it means more than one cap on more than one container.)

It is another object of the present invention to provide the method as defined above, additionally comprising step of extracting said fluid simultaneously from both of said containers.

It is another object of the present invention to provide the method as defined above, wherein said system additionally comprising step of extracting said fluid simultaneously from both of said containers each of which has different rate of flow or different pressure.

It is another object of the present invention to provide the method as defined above, wherein said fluid extracting means are selected from a group consisting of pumping means for withdrawing fluid out of said container; pressure applying means adapted to apply pressure on said container such that fluid is extracted from the same; and any combination thereof.

It is another object of the present invention to provide the method as defined above, wherein said step of extracting said fluid comprises one of a group consisting of (a) pumping said fluid from said containers; (b) applying pressure on said container such that fluid is extracted from the same; and any combination thereof.

It is another object of the present invention to provide the method as defined above, wherein said pressure applying means are selected from a group consisting of a membrane encapsulating at least one of said containers of fluid, and squeezing means adapted to apply squeezing pressure on at least one of said containers and any combination thereof.

It is another object of the present invention to provide the method as defined above, wherein said squeezing means are selected from at least one of pneumatic, hydrostatic, and compression of at least one of the containers.

It is another object of the present invention to provide the method as defined above, further comprising a step of using said fluid regulating means to block flow of fluid from said first container at any time that flow is permitted from another container.

It is another object of the present invention to provide the method as defined above, further comprising a step of determining the weight of each of said of said containers in order to determine the amount of fluid within.

It is another object of the present invention to provide the method as defined above, further comprising a step of notifying the user upon the occurrence of at least one condition chosen from the group consisting of (a) the beginning of pumping of fluid from the Nth of said N containers; (b) a failure of a predetermined component; (c) a drop in the rate of flow of fluid below a predetermined threshold; (d) a drop in the level of fluid in a predetermined container of said N containers below a predetermined threshold; (e) time from the beginning of the procedure; (f) number of containers being used; and any combination thereof.

It is another object of the present invention to provide the method as defined above, further comprising additional steps of:

ejecting said spike of said first fluid transfer head, thereby creating a fluid connection between said first container and said outlet; and, extracting fluid from said first container until the level of fluid within said first container drops by a predetermined amount, by either pumping said fluid or applying pressure on the same so as to extract fluid;

wherein said additional steps are performed after the level of fluid in said other container drops to said predetermined value and before the commencement of pumping of fluid from the following container.

It is another object of the present invention to provide the method as defined above, further comprising additional steps of:

fixing the height of said first fluid transfer head to the height of another container from which pumping has not yet commenced;

ejecting said spike of said first fluid transfer head, thereby creating a fluid connection between the interior of said another container and said single outlet;

either pumping fluid or applying pressure on said another container until the amount of fluid within said drops by a predetermined amount; and, repeating sequentially steps of fixing the height of each fluid transfer head to the height of a container from which pumping has not yet commenced, ejecting the spike therefrom, and pumping fluid from the current container for each of said fluid transfer heads until the level of fluid within each of said containers has dropped by a predetermined amount.

It is another object of the present invention to provide the method as defined above, additionally comprising at least one step of (a) controlling the rate of flow of fluid through said irrigation system according to a predetermined protocol; or (b) controlling the movement of said at least one fluid transfer head; (c) controlling the activation of the same; and any combination thereof.

It is another object of the present invention to provide the method as defined above, additionally comprising step of withdrawing said fluid from at least one of said containers of fluid in a predetermined rate of flow to an outer tubing system.

It is another object of the present invention to provide the method as defined above, wherein said containers are disposed in a predetermined configuration.

It is another object of the present invention to provide the method as defined above, wherein said predetermined configuration is selected from a group consisting of linear shape, radial shape, ellipsoidal shape, square shape, triangular shape, hexagonal shape, pentagonal shape, any 2D shape, any 3D shape and any combination thereof.

It is another object of the present invention to provide the method as defined above, additionally comprising step of regulating either the rate of transfer of fluid from said reservoir system to each of said fluid transfer heads or the pressure at which said fluid is transferred from said reservoir system to each of said fluid transfer heads.

It is another object of the present invention to provide the method as defined above, additionally comprising at least one step of (a) controlling the rate of flow of fluid through said irrigation system according to a predetermined protocol; or (b) controlling the movement of said at least one fluid transfer head; (c) controlling the activation of the same; and any combination thereof.

It is another object of the present invention to provide the method as defined above, additionally comprising step of selecting said fluid from a group consisting of gas, liquid and any combination thereof.

It is another object of the present invention to provide the method as defined above, additionally comprising step of selecting said fluid from oxygen; oxygen; anesthetic gas for use as local anesthesia, regional anesthesia and general anesthesia selected from ethers, halogenated ethers, desflurane (2,2,2-trifluoro-1-fluoroethyl-difluoromethyl ether, sevoflurane (2,2,2-trifluoro-1-[trifluoromethyl]ethyl fluoromethyl ether), and isoflurane (2-chloro-2-(difluoromethoxy)-1,1,1-trifluoro-ethane); blood; saline; glycine; water; plasma; medicament and any combination thereof.

It is another object of the present invention to provide the method as defined above, additionally comprising step of delivering several substantially different fluids.

It is another object of the present invention to provide the method as defined above, additionally comprising step of providing said substantially different fluids to said patient in substantially the same amounts, different amounts, substantially the same rates, different rates, and any combination thereof.

It is another object of the present invention to provide the method as defined above, additionally comprising step of providing said reservoir system with:
- a plurality of N support shelves adapted to support each of said containers of said fluid;
- support means adapted to support said shelves and to maintain a predetermined distance and orientation between each pair of shelves; and,
- a plurality of at least N slots in said shelf support means, said slots positioned such that at least one slot is located proximate to each of said N shelves.

It is another object of the present invention to provide the method as defined above, wherein said support is selected from a group consisting of shelf, drawer, receptacle, sliding receptacle and any combination thereof.

It is another object of the present invention to provide the method as defined above, additionally comprising step of providing said containers as bags made of a flexible material.

It is another object of the present invention to provide the method as defined above, additionally comprising step of providing said containers as bags made of a rigid material.

It is another object of the present invention to provide the method as defined above, wherein said rigid material is plastic bottles, ceramic bottles, metal bottles, and any combination thereof.

It is another object of the present invention to provide the method as defined above, additionally comprising step of constantly monitoring the amount of fluid extracted from said reservoir system and of reporting the value of said determination.

It is another object of the present invention to provide the method as defined above, additionally comprising step of providing said irrigation system with weight measuring and reporting means adapted to determine the weight of each of said containers and to report the value of said determination.

It is another object of the present invention to provide the method as defined above, additionally comprising step of providing said irrigation system with volume measuring and reporting means adapted to determine the volume of each of said containers and to report the value of said determination.

It is another object of the present invention to provide the method as defined above, additionally comprising step of providing said irrigation system with at least one image sensor adapted to provide real time images of each of said containers.

It is another object of the present invention to provide the method as defined above, additionally comprising step of selecting said image sensor from a group consisting of a camera, a video and any combination thereof.

It is another object of the present invention to provide the method as defined above, additionally comprising step of providing said irrigation system with at least one processing unit in communication with said at least one image sensor, adapted for real time image processing of said image such that either the volume or the weight of each of said containers is provided.

It is another object of the present invention to provide the method as defined above, additionally comprising step of allowing rotation of each of said supports about an axis parallel to its longitudinal axis, said support rotation means further adapted to allow each of said supports to be fixed at an angle chosen by the operator of said irrigation system.

It is another object of the present invention to provide the method as defined above, additionally comprising step of selecting said angle is in a range of about 0 degrees to about 90 degrees.

it is another object of the present invention to provide the method as defined above, additionally comprising step of providing each of said containers comprises a neck and a nipple, and further wherein said irrigation system further comprises at least one connector between said container and said fluid transfer head, wherein said connector is reversibly coupled to said irrigation system and comprises:
- a lower section comprising two arcs, the first of which is of a diameter and depth adapted to support said neck, and the second of which is of a diameter and depth adapted to support said nipple, the distance between the centers of said arcs substantially equal to the distance between the centers of said neck and said nipple; and,
- an upper section hingedly connected to said lower section, said upper section comprising two arcs of diameters substantially identical to those of the corresponding arcs of said lower section, said two arcs disposed such that closure of said hinged connection forms at least one circular hollow passageway passing through said connector.

It is another object of the present invention to provide the method as defined above, additionally comprising means adapted to fix said containers in place, to verify said containers are in place and any combination thereof.

It is another object of the present invention to provide the method as defined above, additionally comprising step of providing said fluid transfer system with:
- fluid transfer head support means adapted to support said fluid transfer heads, said fluid transfer head support means adapted to allow vertical motion, radial motion and any combination thereof of at least one of said fluid transfer heads.

It is another object of the present invention to provide the method as defined above, additionally comprising step of providing each of said fluid transfer heads with:
- a spike;
- flexible tubing in fluid contact with said spike;
- ejecting and retracting means for ejecting at least one of said spike and said fluid transfer head a predetermined minimum distance along the horizontal axis from a resting position to an ejected position and for retracting said at least one of said spike and said fluid transfer head from said ejected position to said resting position.
- height fixing means adapted to fix the vertical position of said fluid transfer head.

It is another object of the present invention to provide the irrigation system as defined above, wherein said flexible tubing further comprises at least one internal reservoir for accommodating said fluid and for delivering said fluid while said fluid transfer head linearly moves along said main longitudinal axis.

It is another object of the present invention to provide the irrigation system as defined above, wherein said flexible tubing further comprises at least one internal reservoir for accommodating said fluid and for delivering said fluid while said fluid transfer head radially moves around said main longitudinal axis.

It is another object of the present invention to provide the method as defined above, additionally comprising step of height fixing the vertical position of said fluid transfer head along said main longitudinal axis of said reservoir system.

It is another object of the present invention to provide the method as defined above, additionally comprising step of providing at least one of said fluid transfer heads with an actuator in mechanical contact with said fluid transfer head support means and in electronic connection with said control means, said actuator adapted to engage with said fluid transfer head support means, whereby actuation of said actuator by a command from said control means causes vertical motion of said fluid transfer head along the vertical axis of said fluid transfer support means through a distance determined by said control means.

It is another object of the present invention to provide the method as defined above, additionally comprising step of selecting said actuator from a group consisting of stepper motor, voice command actuator, motion detector and any combination thereof.

It is another object of the present invention to provide the method as defined above, additionally comprising step of providing said fluid regulating means with:
  pressure applying means mounted proximate to said flexible tubing in fluid contact with said spike; and,
  extending and retracting means in mechanical contact with said pressure applying means, said extending and retracting means adapted to reversibly extend said pressure applying means.

It is another object of the present invention to provide the method as defined above, wherein said extending and retracting means comprise a retractable spring.

It is another object of the present invention to provide the method as defined above, wherein said extending and retracting means are actuated by a means chosen from the group consisting of manual, mechanical, electrical, pneumatic, electromechanical, electropneumatic and any combination thereof.

It is another object of the present invention to provide the method as defined above, wherein said fluid regulating means comprises at least one selected from a group consisting of a pinch valve, a wheel-like shaped element adapted to apply pressure, and any combination thereof.

It is another object of the present invention to provide the method as defined above, additionally comprising step of selecting said pumping system to comprise a peristaltic pump.

It is another object of the present invention to provide the method as defined above, wherein said pumping system comprises a single inlet, and further wherein at least two of said containers are in fluid connection with said single inlet.

It is another object of the present invention to provide the method as defined above, wherein two of said containers are in fluid connection with a "Y" joint located downstream of said fluid transfer heads.

It is another object of the present invention to provide the method as defined above, additionally comprising step of providing said irrigation system with: at least one additional container in fluid connection with said pumping means;
  means for opening and closing said fluid connection; and,
  a rack adapted to hang said additional containers.

It is another object of the present invention to provide the method as defined above, additionally comprising step of providing said irrigation system with an emergency shutoff switch adapted to halt flow of fluid through said irrigation system.

It is another object of the present invention to provide the method as defined above, additionally comprising step of preventing over pressure of said fluid in said irrigation system.

It is another object of the present invention to provide the method as defined above, wherein said over pressure is prevented by means of at least one pressure sensor located in said pumping system.

It is another object of the present invention to provide the method as defined above, wherein said over pressure is prevented by means of at least one pressure sensor in communication with said outer tubing system.

It is another object of the present invention to provide the method as defined above, wherein said over pressure is prevented by means of at least one pressure sensor located within said outer tubing system.

It is another object of the present invention to provide the method as defined above, wherein said over pressure is prevented by means of pre-setting the maximum pressure to which said pump can reach.

It is another object of the present invention to provide the irrigation system as defined above, wherein said over pressure is prevented by means of at least one pressure sensor surrounding at least a portion of said outer tubing system.

It is another object of the present invention to provide the irrigation system as defined above, wherein said over pressure is prevented by means of limiting the pumping system to predetermined values.

It is another object of the present invention to provide the method as defined above, additionally comprising step of providing said irrigation system with removing means for removing a protective cover or cap from said container.

It is another object of the present invention to provide the method as defined above, additionally comprising step of providing said irrigation system with an automatic collecting means adapted to collect said cover or cap from said irrigation system.

It is another object of the present invention to provide the method as defined above, wherein said removing means comprises cutting means and actuating means adapted to actuate said cutting means.

It is another object of the present invention to provide the method as defined above, wherein said removing means comprise pressure applying means, adapted to apply pressure on said cover or cap by at least one of a group consisting of pulling, pushing and twisting said cover or cap.

According to another embodiment a substantially continuous flow of fluid is provide. In the above disclosure, a reservoir of fluid is provided. According to another embodiment of the present invention, the at least one spike is maneuvered from one container to the other, without having any reservoir container supporting said fluid to the patient in the intermediate time (when the spike has been extracted from one container to the time the spike has penetrated/ejected a second container).

Alternatively there can be several spikes being maneuvered from one container to the other; such that when one container is being emptied from fluid, the spike is maneuver to a second container.

The use of the invention is now further illustrated by a series of non-limiting examples, which give specific protocols for the use of the invention to provide a constant automatic flow of fluid from the reservoir system to the point of use. One skilled in the art will recognize that the general principles of the protocols illustrated can be extended to numbers of containers and fluid transfer heads other than those specifically given in the examples. Hence, these examples are given solely to illustrate the general principles of the use of the apparatus, and all other combinations of components that rely on these principles are envisioned by the inventor as being within the scope of the invention.

EXAMPLE 1

One embodiment of a typical protocol for a system comprising three containers, labeled "Bag 1," "Bag 2," and "Bag 3," respectively, and at least two fluid transfer heads, labeled "Head 1" and "Head 2," respectively, is herein described. The procedure begins (Step 0) with the needle from Head 1 being inserted into bag 1, and the pinch valve closed (i.e. the flow regulating means is set to prevent flow of fluid). In Step 1, the pinch valve is retracted, and fluid pumped from Bag 1 until the fluid level in the bag is lowered to a predetermined amount (typically between 0 and 50% of its initial volume). At this point (Step 2), the needle from Head 2 is inserted into Bag 2, the pinch valve from Head 2 opened and the pinch valve from Head 1 closed, stopping flow from Bag 1 and beginning flow from Bag 2. Step 3 of the protocol occurs when the amount of fluid in Bag 2 decreases to a predetermined fraction of its original amount. At this point, the pinch valve from Head 1 is reopened and the pinch valve from Head 2 is closed restoring flow from Bag 1, and the needle from Head 2 is retracted. Head 2 is then moved so that it is proximate to Bag 3, while flow continues from Bag 1, lowering the fluid content therein by a nominal amount during the transfer of Head 2 to Bag 3. At this point (Step 4), the needle from Head 2 is inserted into Bag 3 and the pinch valve opened, while the pinch valve from Head 1 is closed, so that flow commences from Bag 3 while being stopped from Bag 1. Finally (Step 5), when the amount of fluid in Bag 3 drops to a predetermined amount, the pinch valve from Head 2 is closed, the pinch valve from Head 1 reopened, and flow restored from Bag 1. Bag 1 can be emptied entirely, or Bags 2 and 3 can be replaced with full containers and the process started anew; Bag 1 can be replaced at any time while flow is occurring from one of the other containers.

This protocol is summarized in Table 1 for the case in which Bags 2 and 3 are substantially completely emptied during the protocol, and the nominal drop in the fluid level in Bag 1 during the transfer of the Head 2 from container to container is defined as "S."

TABLE 1

| | Head 1 | | Head 2 | | % Contents of Bag in the end of the process | | |
|---|---|---|---|---|---|---|---|
| Step | Needle | Pinch valve | Needle | Pinch valve | BAG 1 | BAG 2 | BAG 3 |
| 0 | IN Bag 1 | Pressing | OUT | Pressing | 100% | 100% | 100% |
| 1 | IN Bag 1 | Retracted | OUT | Pressing | 50-0% | 100% | 100% |
| 2 | IN Bag 1 | Pressing | IN Bag 2 | Retracted | 50-0% | 100-0% | 100% |
| 3 | IN Bag 1 | Retracted | OUT | Pressing | (50-δ)% | 0% | 100% |
| 4 | IN Bag 1 | Pressing | IN Bag 3 | Retracted | (50-δ)% | 0% | 100-0% |
| 5 | IN Bag 1 | Retracted | IN Bag 3 | Pressing | (50-δ)-0% | 0% | 0% |

EXAMPLE 2

The basic principle of the protocol presented in this example is identical to that of the previous example except that four containers are used instead of three. The steps in the protocol are summarized in Table 2.

TABLE 2

| | Head 1 | | Head 2 | | % Contents of Bag in the end of the process | | | |
|---|---|---|---|---|---|---|---|---|
| Step | Needle | Pinch valve | Needle | Pinch valve | BAG 1 | BAG 2 | BAG 3 | BAG 4 |
| 0 | IN Bag 1 | Pressing | OUT | Pressing | 100% | 100% | 100% | 100% |
| 1 | IN Bag 1 | Retracted | OUT | Pressing | 0-50% | 100% | 100% | 100% |
| 2 | IN Bag 1 | Pressing | IN Bag 2 | Retracted | 0-50% | 100-0% | 100% | 100% |
| 3 | IN Bag 1 | Retracted | OUT | Pressing | (50-δ)% | 0% | 100% | 100% |
| 4 | IN Bag 1 | Pressing | IN Bag 3 | Retracted | (50-δ)% | 0% | 0-100% | 100% |
| 5 | IN Bag 1 | Retracted | OUT | Pressing | (50-nδ)% | 0% | 0% | 100% |
| 6 | IN Bag 1 | Pressing | IN Bag 4 | Retracted | (50-nδ)% | 0% | 0% | 0-100% |
| 7 | IN Bag 1 | Retracted | OUT | Pressing | (50-δ)-0% | 0% | 0% | 0% |

It will be clear to one skilled in the art that the protocol can be performed for any number of containers and for any arbitrary value of the predetermined fluid drop necessary to advance the protocol to the succeeding step.

EXAMPLE 3

In other embodiment of the invention, both fluid transfer heads are moved from container to container during the course of its use. In this example fluid transfer head 1 can extracted fluid only from bag in shelves no. 1, 2 and 3 if there are bags available there while fluid transfer head 2 is can only extracted fluid from bag in shelves no. 4, 5 and 6 in there are bags available. In this example bags are available in shelves no. 1, 2 and 4. The procedure begins (Step 0) with the needle from Head 1 being inserted into bag 1, and the pinch valve closed (i.e. the flow regulating means is set to prevent flow of fluid). In Step 1, the pinch valve is retracted, and fluid pumped from Bag 1 until the fluid level in the bag is lowered to a predetermined amount (typically between 0 and 10% of its initial volume). At this point (Step 2), the needle from Head 2 is inserted into another container (in the specific case of this example, Bag 4), the pinch valve from Head 2 opened and the pinch valve from Head 1 closed, thus enabling flow from Bag 4. When the fluid level in Bag 4 drops by a predetermined amount, the needle from Head 1 is retracted. Head 1 is then moved so that it is proximate to Bag 2, while flow continues from Bag 4, lowering the fluid content therein by a nominal amount during the transfer of Head 1 to Bag 2. At this point (Step 3), the needle from Head 1 is inserted into Bag 2 and the pinch valve opened, while the pinch valve from Head 2 is closed, and fluid flow commences from Bag 2. The steps of this protocol are summarized in Table 3.

TABLE 3

| | Head 1 | | Head 2 | | % Contents of Bag in the end of the process | | |
| --- | --- | --- | --- | --- | --- | --- | --- |
| Step | Needle | Pinch valve | Needle | Pinch valve | BAG 1 | BAG 2 | BAG 4 |
| 0 | IN Bag 1 | Pressing | OUT | Pressing | 100% | 100% | 100% |
| 1 | IN Bag 1 | Retracted | OUT | Pressing | 0-10% | 100% | 100% |
| 2 | IN Bag 1 | Pressing | IN Bag 4 | Retracted | 0-10% | 100% | 100-0% |
| 3 | IN Bag 2 | Retracted | OUT | Pressing | 0% | 100% | 0% |
| 4 | OUT | | | | 0% | 0% | 0% |

It will be clear to one skilled in the art that this "tandem" protocol will work equally well for any arbitrary number of containers.

We claim:

1. An irrigation system for providing a continuous and controlled flow of a fluid, wherein said system comprises:
   a reservoir system comprising a plurality of containers of fluid; said reservoir system is characterized by a main longitudinal axis;
   a fluid transfer system in fluid connection with said reservoir system, said fluid transfer system comprising: at least one fluid transfer head, adapted to transfer fluid from one of said plurality of containers to an external tubing system;
   wherein each of said fluid transfer heads is characterized by a mechanism adapted to linearly move each of said fluid transfer heads along said main longitudinal axis;
   wherein each of said containers comprises a neck and a nipple,
   wherein said irrigation system further comprises at least one connector between said container and said fluid transfer head,
   wherein said connector is reversibly coupled to said irrigation system and comprises:
      a lower section comprising two arcs, the first of which is of a diameter and depth adapted to support said neck, and the second of which is of a diameter and depth adapted to support said nipple, the distance between the centers of said arcs substantially equal to the distance between the centers of said neck and said nipple; and,
      an upper section hingedly connected to said lower section,
      said upper section comprising two arcs of diameters substantially identical to those of the corresponding arcs of said lower section, said two arcs disposed such that closure of said hinged connection forms at least one circular hollow passageway passing through said connector;
   wherein said system additionally comprising means adapted to fix said containers in place, to verify said containers are in place and any combination thereof.

2. The irrigation system of claim 1, wherein at least one of the following is being held true (a) said fluid transfer system further comprising fluid regulating means, adapted to regulate either the rate of transfer of fluid from said reservoir system to each of said fluid transfer heads or the pressure at which said fluid is transferred from said reservoir system to each of said fluid transfer heads; (b) said system further comprising a control system adapted to control at least one selected from a group consisting of (i) the rate of flow of fluid through said irrigation system according to a predetermined protocol; (ii) the movement of said at least one fluid transfer head; (iii) the activation of the same; and any combination thereof; (c) said system additionally comprising pressure building system selected from pumping means adapted to withdraw said fluid from at least one of said containers; or pressure applying means adapted to apply pressure on at least one of said containers; (d) said system further comprising a pumping system in fluid connection with said fluid transfer system, adapted to withdraw said fluid from at least one of said containers of fluid in a predetermined rate of flow to an outer tubing system; (e) said fluid transfer system comprises at least at least two fluid transfer heads; (f) said at least one fluid transfer head comprises at least one internal reservoir for accommodating said fluid and for delivering said fluid while said fluid transfer head linearly moves along said main longitudinal axis; and any combination thereof.

3. The irrigation system of claim 1, wherein said system further comprising pressure applying means adapted to apply pressure on at least one of said containers of fluid so as to enable a predetermined rate of flow from at least one of said containers to an outer tubing system; further wherein said pressure applying means is selected from a group consisting of a membrane encapsulating at least one of said containers of fluid, squeezing means adapted to apply squeezing pressure on at least one of said containers and any combination thereof and any combination thereof; further wherein said squeezing means are selected from pneumatic compression of at least one of the containers, hydrostatic compression of at least one of the containers, and any combination thereof.

4. The irrigation system of claim 1, wherein said fluid is selected from a group consisting of gas, liquid and any combination thereof; wherein said fluid is selected from oxygen; anesthetic gas for use as local anesthesia, regional anesthesia and general anesthesia selected from ethers, halogenated ethers, desflurane (2,2,2-trifluoro-1-fluoroethyl-difluoromethyl ether, sevoflurane (2,2,2-trifluoro-1-[trifluoromethyl] ethyl fluoromethyl ether), and isoflurane (2-chloro-2-(difluoromethoxy)-1,1,1-trifluoro-ethane); blood; saline; glycine; water; plasma; medicament and any combination thereof.

5. The irrigation system of claim 4, wherein said system is adapted to deliver several substantially different fluids; wherein said substantially different fluids are provided to said patient in substantially the same amounts, different amounts, substantially the same rates, different rates, and any combination thereof.

6. The irrigation system of claim 1, wherein at least one of the following is being held true (a) said at least one fluid transfer head comprises at least one internal reservoir for accommodating said fluid and for delivering said fluid while said fluid transfer head radially moves around said main longitudinal axis; (b) said containers are bags made of a flexible material; (c) said containers are made of a rigid material; said rigid material is glass, plastic, ceramic, metal, and any combination thereof; (d) said reservoir system further comprising monitoring means adapted to constantly monitor the amount of fluid extracted from said reservoir system and/or the amount of fluid remained in said reservoir system and reporting means adapted to report the value of said determination; (e) said reservoir system further comprises weight measuring and reporting means adapted to determine the weight of each of said containers and to report the value of said determination; (f) said reservoir system further comprises volume measuring and reporting means adapted to determine the volume of each of said containers and to report the value of said determination; and any combination thereof.

7. The irrigation system of claim 1, wherein said reservoir system comprises: a plurality of N support shelves adapted to support each of said containers of said fluid; support means adapted to support said shelves and to maintain a predetermined distance and orientation between each pair of shelves; and, a plurality of at least N slots in said shelf support means, said slots positioned such that at least one slot is located proximate to each of said N shelves; further wherein said support is selected from a group consisting of shelf, drawer, receptacle a sliding receptacle, chamber and any combination thereof.

8. The irrigation system of claim 1, wherein said reservoir system further comprises at least one image sensor adapted to provide real time images of each of said containers; further wherein said image sensor is selected from a group consisting of a camera, a video and any combination thereof.

9. The irrigation system of claim 1, wherein at least one of the following is being held true (a) said reservoir system further comprises at least one processing unit in communication with said at least one image sensor, adapted for real time image processing of said image such that either the volume or the weight of each of said containers is provided; (b) said system further comprising support rotation means adapted to allow rotation of each of said supports about an axis parallel to its longitudinal axis, said support rotation means further adapted to allow each of said supports to be fixed at an angle chosen by the operator of said irrigation system; said angle is adapted to be fixed prior to said irrigation, during said irrigation and any combination thereof; said angle is in a range of about 0 degrees to about 90 degrees; (c) said fluid transfer system further comprises fluid transfer head support means adapted to support said fluid transfer heads; said fluid transfer head support means adapted to allow vertical motion, radial motion and any combination thereof of at least one of said fluid transfer heads; and any combination thereof.

10. The irrigation system of claim 9, wherein each of said fluid transfer heads comprises: a spike; flexible tubing in fluid contact with said spike; ejecting and retracting means for ejecting at least one of said spike and said fluid transfer head a predetermined minimum distance along the horizontal axis from a resting position to an ejected position and for retracting said at least one of said spike and said fluid transfer head from said ejected position to said resting position; height fixing means adapted to fix the vertical position of said fluid transfer head; further wherein at least one of the following is being held true: (a) said flexible tubing further comprises at least one internal reservoir for accommodating said fluid and for delivering said fluid while said fluid transfer head linearly moves along said main longitudinal axis; (b) said flexible tubing further comprises at least one internal reservoir for accommodating said fluid and for delivering said fluid while said fluid transfer head radially moves around said main longitudinal axis; (c) said system additionally comprising height fixing means adapted to fix the vertical position of said fluid transfer head or heads along said main longitudinal axis of said reservoir system; (d) at least one of said fluid transfer heads further comprises an actuator in mechanical contact with said fluid transfer head support means and in electronic connection with said control means, said actuator adapted to engage with said fluid transfer head support means, whereby actuation of said actuator by a command from said control means causes vertical motion of said fluid transfer head along the vertical axis of said fluid transfer support means through a distance determined by said control means; (e) said actuator comprises at least one selected from a group consisting of stepper motor, voice command actuator, motion detector and any combination thereof.

11. The irrigation system of claim 2, wherein said fluid regulating means comprises: pressure applying means mounted proximate to said flexible tubing in fluid contact with said spike; and, extending and retracting means in mechanical contact with said pressure applying means, said extending and retracting means adapted to reversibly extend said pressure applying means further wherein at least one of the following is being held true (a) said fluid regulating means is adapted to activate or de-activate fluid flow in said irrigation system; (b) said extending and retracting means comprise a retractable spring; (c) said extending and retracting means are actuated by a means chosen from the group consisting of manual means, mechanical means, electrical means, pneumatic means, electromechanical means, electropneumatic means and any combination thereof; (d) said fluid regulating means comprises at least one selected from a group consisting of a pinch valve, a wheel-like shaped element adapted to apply pressure, and any combination thereof.

12. The irrigation system of claim 2, wherein said pumping system comprises a peristaltic pump; further wherein said pumping system comprises a single inlet, and further wherein at least two of said containers are in fluid connection with said single inlet; wherein two of said containers are in fluid connection with a "Y" joint located downstream of said fluid transfer heads.

13. The irrigation system of claim 2, wherein said control system comprises a computer in communication with at least one of said reservoir system, said fluid transfer system, and said pumping system, and further wherein said control system is adapted to direct the flow of fluid through said system.

14. The irrigation system of claim 1, further comprising: at least one additional container in fluid connection with said pumping means; means for opening and closing said fluid connection; and, a rack adapted to hang said additional containers.

15. The irrigation system of claim 1, further comprising an emergency shutoff switch adapted to halt flow of fluid through said irrigation system.

16. The irrigation system of claim 1, wherein said control system is adapted to prevent over pressure of said fluid in said irrigation system; wherein at least one of the following is being held true: (a) said over pressure is prevented by means of at least one pressure sensor located in said pumping system; (b) said over pressure is prevented by means of at least one pressure sensor in communication with said outer tubing system; (c) said over pressure is prevented by means of at least one pressure sensor located within said outer tubing system; (d) said over pressure is prevented by means of at least one pressure sensor surrounding at least a portion of said outer tubing system; (e) said over pressure is prevented by means of limiting the pumping system to predetermined values; and any combination thereof.

17. The irrigation system of claim 1, further including removing means for removing a protective cover or cap from said container; wherein at least one of the following is being held true: (a) said system additionally comprising at least one holder, said at least one holder enabled to contain caps and covers removed from none or more of a group consisting of fluid containers, spikes, and fluid transfer heads during operation of said system; (b) said removing means comprise cutting means and actuating means adapted to actuate said cutting means; (c) said removing means comprise pressure applying means, adapted to apply pressure on said cover or cap by at least one of a group consisting of pulling, pushing, and twisting said cover or cap; and any combination thereof.

18. The irrigation system of claim 1, wherein at least one of the following is being held true (a) said fluid transfer head additionally comprises a connector, said connector configured such that said spike can not be coupled to said fluid transfer head before removal of protective covers from said spike; (b) said system is enabled to provide continuous and controlled flow of a fluid to a plurality of patients; wherein said system is enabled to provide continuous and controlled flow of a plurality of fluids to a plurality of patients.

* * * * *